United States Patent
Benetti et al.

(10) Patent No.: US 6,315,717 B1
(45) Date of Patent: *Nov. 13, 2001

(54) SURGICAL INSTRUMENTS FOR STABILIZING THE BEATING HEART DURING CORONARY ARTERY BYPASS GRAFT SURGERY

(75) Inventors: Federico J. Benetti, Rosario (AR); Charles S. Taylor, San Francisco, CA (US); Ivan Sepetka, Los Altos, CA (US); Amr Salahieh, Campbell, CA (US); Robert C. Glines, Cameron Park, CA (US); William N. Aldrich, Redwood City, CA (US); Brent Regan, Davis, CA (US); John J. Frantzen, Copperopolis, CA (US)

(73) Assignee: Cardiothoracic Systems, Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/550,447

(22) Filed: Apr. 17, 2000

Related U.S. Application Data

(62) Division of application No. 09/099,855, filed on Jun. 18, 1998, now Pat. No. 6,050,266, which is a division of application No. 08/603,758, filed on Feb. 20, 1996, now Pat. No. 5,894,843.

(51) Int. Cl.[7] ........................................................ A61B 1/32
(52) U.S. Cl. ........................................... 600/210; 600/235
(58) Field of Search ..................................... 600/201, 204, 600/210, 226, 227, 228, 229, 231, 232, 233, 235, 37; 606/1

(56) References Cited

U.S. PATENT DOCUMENTS

Re. 34,150   12/1992   Santilli et al. .
D. 421,803   3/2000    Koros et al. .
452,131      5/1891    Haughawout .

(List continued on next page.)

FOREIGN PATENT DOCUMENTS 90 04513      6/1990   (DE) .
0 293 760 A2  12/1988  (EP) .
0 293 760 A3  12/1988  (EP) .

(List continued on next page.)

OTHER PUBLICATIONS

"Weck Surgical Instruments and Products," Pilling Weck Catalog, pre–Feb., 1996, pp. B50–B54.*

"Miltex Surgical Instruments," Miltex Surgical Instruments Company, Inc. Catalog, pre–Feb., 1996, pp. 298–299.*

(List continued on next page.)

*Primary Examiner*—Jeffrey A. Smith
(74) *Attorney, Agent, or Firm*—Alan W. Cannon; Bozicevic, Field & Francis LLP

(57) ABSTRACT

Methods and devices used to stabilize a beating heart during a surgical procedure on the heart are disclosed. The stabilizing device is introduced through an opening through the chest and brought into contact with the beating heart, and by exerting a stabilizing force on the device, the motion of the heart caused by the contractions of the heart muscles is effectively eliminated. Accordingly, the heart is stabilized and movement of the site of the surgery is minimized. Typically, in separate steps, a surgeon contacts the heart with the stabilizing device, assesses the degree of movement of the anastomosis site, and exerts a force with a stabilizing device such that the contractions of the beating heart causes only minimal excess motion at the surgery site. The stabilizing device may be attached to a rigid support or may be attached to a semi-rigid support which is rendered motionless mechanically, chemically or by human intervention.

24 Claims, 14 Drawing Sheets

U.S. PATENT DOCUMENTS

| | | |
|---|---|---|
| 810,675 | 1/1906 | Richter . |
| 1,706,500 | 3/1929 | Smith . |
| 2,296,793 | 9/1942 | Kirschbaum . |
| 2,590,527 | 3/1952 | Fluck . |
| 2,693,795 | 11/1954 | Grieshaber . |
| 2,863,444 | 12/1958 | Winsten . |
| 3,392,722 | 7/1968 | Jorgensen . |
| 3,683,926 | 8/1972 | Suzuki . |
| 3,720,433 | 3/1973 | Rosfelder . |
| 3,783,873 | 1/1974 | Jacobs . |
| 3,858,926 | 1/1975 | Ottenhues . |
| 3,882,855 | 5/1975 | Schulte et al. . |
| 3,983,863 | 10/1976 | Janke et al. . |
| 4,047,532 | 9/1977 | Phillips et al. . |
| 4,048,987 | 9/1977 | Hurson . |
| 4,049,000 | 9/1977 | Williams . |
| 4,049,002 | 9/1977 | Kletschka et al. . |
| 4,052,980 | 10/1977 | Grams et al. . |
| 4,226,228 | 10/1980 | Shin et al. . |
| 4,230,119 | 10/1980 | Blum . |
| 4,306,561 | 12/1981 | de Medinaceli . |
| 4,366,819 | 1/1983 | Kaster . |
| 4,368,736 | 1/1983 | Kaster . |
| 4,421,107 | 12/1983 | Estes et al. . |
| 4,428,368 | 1/1984 | Torii . |
| 4,434,791 | 3/1984 | Darnell . |
| 4,461,284 | 7/1984 | Fackler . |
| 4,492,229 | 1/1985 | Grunwald . |
| 4,627,421 | 12/1986 | Symbas et al. . |
| 4,637,377 | 1/1987 | Loop . |
| 4,646,747 | 3/1987 | Lundback . |
| 4,688,570 | 8/1987 | Kramer et al. . |
| 4,702,230 | 10/1987 | Pelta . |
| 4,718,418 | 1/1988 | L'Esperance, Jr. . |
| 4,726,356 | 2/1988 | Jablonski . |
| 4,726,358 | 2/1988 | Brady . |
| 4,736,749 | 4/1988 | Lundback . |
| 4,747,395 | 5/1988 | Brief . |
| 4,754,746 | 7/1988 | Cox . |
| 4,803,984 | 2/1989 | Narayanan et al. . |
| 4,808,163 | 2/1989 | Laub . |
| 4,829,985 | 5/1989 | Couetil . |
| 4,852,552 | 8/1989 | Chaux . |
| 4,854,318 | 8/1989 | Solem et al. . |
| 4,858,552 | 8/1989 | Glatt et al. . |
| 4,863,133 | 9/1989 | Bonnell . |
| 4,865,019 | 9/1989 | Phillips . |
| 4,884,559 | 12/1989 | Collins . |
| 4,925,443 | 5/1990 | Heilman et al. ........................ 600/16 |
| 4,949,707 | 8/1990 | LeVahn et al. . |
| 4,955,896 | 9/1990 | Freeman . |
| 4,962,758 | 10/1990 | Lasner et al. . |
| 4,971,037 | 11/1990 | Pelta . |
| 4,973,300 | 11/1990 | Wright ................................... 600/37 |
| 4,989,587 | 2/1991 | Farley . |
| 4,991,578 | 2/1991 | Cohen . |
| 4,993,862 | 2/1991 | Pelta . |
| 5,009,660 | 4/1991 | Clapham . |
| 5,011,469 | 4/1991 | Buckberg et al. . |
| 5,025,779 | 6/1991 | Bugge . |
| 5,036,868 | 8/1991 | Berggren et al. . |
| 5,037,428 | 8/1991 | Picha et al. . |
| 5,052,373 | 10/1991 | Michelson . |
| 5,053,041 | 10/1991 | Ansari et al. . |
| 5,080,088 | 1/1992 | LeVahn . |
| 5,098,369 | 3/1992 | Heilman et al. ........................ 600/16 |
| 5,119,804 | 6/1992 | Anstadt . |
| 5,131,905 | 7/1992 | Grooters ................................. 600/17 |
| 5,133,724 | 7/1992 | Wilson, Jr. et al. . |
| 5,159,921 | 11/1992 | Hoover . |
| 5,167,223 | 12/1992 | Koros et al. . |
| 5,171,254 | 12/1992 | Sher . |
| 5,231,974 | 8/1993 | Giglio et al. . |
| 5,287,861 | 2/1994 | Wilk . |
| 5,293,863 | 3/1994 | Zhu et al. . |
| 5,300,087 | 4/1994 | Knoepfler . |
| 5,318,013 | 6/1994 | Wilk . |
| 5,336,252 | 8/1994 | Cohen . |
| 5,382,756 | 1/1995 | Dagan . |
| 5,383,840 | 1/1995 | Heilman et al. ........................ 600/17 |
| 5,417,709 | 5/1995 | Slater . |
| 5,425,705 | 6/1995 | Evard et al. . |
| 5,437,651 | 8/1995 | Todd et al. . |
| 5,452,733 | 9/1995 | Sterman et al. ...................... 128/898 |
| 5,467,763 | 11/1995 | McMahon et al. . |
| 5,498,256 | 3/1996 | Furnish . |
| 5,503,617 | 4/1996 | Jako . |
| 5,509,890 | 4/1996 | Kazama ................................. 600/37 |
| 5,512,037 | 4/1996 | Russell et al. . |
| 5,514,075 | 5/1996 | Moll et al. ............................ 600/202 |
| 5,514,076 | 5/1996 | Ley . |
| 5,520,610 | 5/1996 | Giglio et al. . |
| 5,529,571 | 6/1996 | Daniel .................................. 600/219 |
| 5,536,251 | 7/1996 | Evard et al. . |
| 5,547,458 | 8/1996 | Ortiz et al. . |
| 5,569,274 | 10/1996 | Rapacki et al. . |
| 5,571,215 | 11/1996 | Sterman et al. . |
| 5,573,496 | 11/1996 | McPherson et al. . |
| 5,607,421 | 3/1997 | Jeevanandam et al. . |
| 5,607,446 | 3/1997 | Beehler et al. . |
| 5,613,937 | 3/1997 | Garrison et al. ..................... 600/201 |
| 5,651,378 | 7/1997 | Matheny et al. . |
| 5,667,480 | 9/1997 | Knight et al. ........................ 600/210 |
| 5,713,951 | 2/1998 | Garrison et al. . |
| 5,727,569 | 3/1998 | Benetti et al. ........................ 128/989 |
| 5,728,151 | 3/1998 | Garrison et al. . |
| 5,730,757 | 3/1998 | Benetti et al. . |
| 5,735,290 | 4/1998 | Sterman et al. . |
| 5,749,892 | 5/1998 | Vierra et al. ......................... 600/204 |
| 5,755,660 | 5/1998 | Tyagi . |
| 5,766,151 | 6/1998 | Valley et al. . |
| 5,772,583 | 6/1998 | Wright et al. . |
| 5,782,746 | 7/1998 | Wright ................................... 600/37 |
| 5,795,291 | 8/1998 | Koros et al. . |
| 5,797,960 | 8/1998 | Steven et al. . |
| 5,799,661 | 9/1998 | Boyd et al. . |
| 5,807,243 | 9/1998 | Vierra et al. ......................... 600/204 |
| 5,813,410 | 9/1998 | Levin . |
| 5,836,311 | 11/1998 | Borst et al. ........................... 128/897 |
| 5,846,187 | 12/1998 | Wells et al. . |
| 5,846,193 | 12/1998 | Wright . |
| 5,846,194 | 12/1998 | Wasson et al. . |
| 5,865,730 | 2/1999 | Fox et al. . |
| 5,868,770 | 2/1999 | Rygaard . |
| 5,875,782 | 3/1999 | Ferrari et al. . |
| 5,876,332 | 3/1999 | Looney . |
| 5,879,291 | 3/1999 | Kolata et al. . |
| 5,882,299 | 3/1999 | Rastegar et al. . |
| 5,885,271 | 3/1999 | Hamilton et al. . |
| 5,888,247 | 3/1999 | Benetti .................................. 623/66 |
| 5,891,017 | 4/1999 | Swindle et al. . |
| 5,894,843 | 4/1999 | Benetti et al. . |
| 5,906,607 | 5/1999 | Taylor et al. ............................ 606/1 |
| 5,908,382 | 6/1999 | Koros et al. . |
| 5,913,876 | 6/1999 | Taylor et al. . |
| 5,927,284 | 7/1999 | Borst et al. ........................... 128/989 |
| 5,944,658 | 8/1999 | Koros et al. . |
| 5,944,736 | 8/1999 | Taylor et al. . |
| 5,947,125 | 9/1999 | Benetti . |
| 5,947,896 | 9/1999 | Sherts et al. . |
| 5,957,835 | 9/1999 | Anderson et al. . |

| | | |
|---|---|---|
| 5,967,972 | 10/1999 | Santilli et al. |
| 5,976,080 | 11/1999 | Farascioni . |
| 5,976,171 | 11/1999 | Taylor . |
| 5,984,865 | 11/1999 | Farley et al. |
| 5,984,867 | 11/1999 | Deckman et al. |
| 6,007,486 | 12/1999 | Hunt et al. |
| 6,010,531 | 1/2000 | Donlon et al. |
| 6,015,378 | 1/2000 | Borst et al. |
| 6,017,304 | 1/2000 | Vierra et al. |
| 6,019,722 | 2/2000 | Spence et al. |
| 6,027,476 | 2/2000 | Sterman et al. |
| 6,029,671 | 2/2000 | Stevens et al. |
| 6,030,340 | 2/2000 | Maffei et al. |
| 6,032,672 | 3/2000 | Taylor . |
| 6,033,362 | 3/2000 | Cohn . |
| 6,036,641 | 3/2000 | Taylor et al. |
| 6,050,266 | 4/2000 | Benetti et al. |
| 6,063,021 | 5/2000 | Hossain et al. |
| 6,071,295 | 6/2000 | Takahashi . |
| 6,099,468 | 8/2000 | Santilli et al. |
| 6,102,854 | 8/2000 | Cartier . |
| 6,139,492 | 10/2000 | Vierra et al. |
| 6,190,311 | 2/2001 | Glines et al. |
| 6,213,941 | 4/2001 | Benetti et al. |

FOREIGN PATENT DOCUMENTS

| | | |
|---|---|---|
| 0 293 760 B1 | 12/1988 | (EP) . |
| 0 630 629 | 5/1994 | (EP) . |
| 668 058A1 | 8/1995 | (EP) . |
| 0 803 228 A1 | 10/1997 | (EP) . |
| 0 993 806 A2 | 4/2000 | (EP) . |
| 473451 | 1/1915 | (FR) . |
| 168216 | 9/1921 | (GB) . |
| 2 233 561 A | 1/1991 | (GB) . |
| 2 267 827 A | 12/1993 | (GB) . |
| WO 87/04081 | 7/1987 | (WO) . |
| WO 94/14383 | 7/1994 | (WO) . |
| WO 94/18881 | 9/1994 | (WO) . |
| WO 95/01757 | 1/1995 | (WO) . |
| WO 95/15715 | 6/1995 | (WO) . |
| WO 95/17127 | 6/1995 | (WO) . |
| WO 96/00033 | 1/1996 | (WO) . |
| WO 97/10753 | 3/1997 | (WO) . |
| WO 97/26828 | 7/1997 | (WO) . |
| WO 97/32514 A2 | 9/1997 | (WO) . |
| WO 97/32514 A3 | 9/1997 | (WO) . |
| WO 97/40752 | 11/1997 | (WO) . |
| WO 98/27869 | 7/1998 | (WO) . |
| WO 98/48703 | 11/1998 | (WO) . |
| WO 98/49947 | 11/1998 | (WO) . |
| WO 99/08585 | 2/1999 | (WO) . |
| WO 99/09892 | 3/1999 | (WO) . |
| WO 99/16367 | 4/1999 | (WO) . |
| WO 00/06041 | 2/2000 | (WO) . |
| WO 00/10466 | 3/2000 | (WO) . |
| WO 00/16367 | 3/2000 | (WO) . |
| WO 00/42920 | 7/2000 | (WO) . |
| WO 00/42921 | 7/2000 | (WO) . |
| WO 00/42935 | 7/2000 | (WO) . |
| WO 00/42936 | 7/2000 | (WO) . |
| WO 00/42937 | 7/2000 | (WO) . |

OTHER PUBLICATIONS

Ancalmo, N. and J. L. Ochsner: "*A Modified Sternal Retractor,*" Ann. Thorac, Surg. 21 (1976) 174.

Angelini, G.D., M.D., "*Simple, Inexpensive Method of Heart Retraction During Coronary Artery Bypass Surgery,*" Ann. Thora. Surg 46:46–247, Aug. 1988.

Angelini, G.D., M.D. et al., "*Fiber–Optic Retractor for Harvesting the Internal Mammary Artery,*" Ann. Thorac. Surg. (1990; 50:314–5).

Antinori, C. et al., "*A Method of Retraction During Reoperative Coronary Operations Using the Favaloro Retractor,*" "The Society of Thoracic Surgeons: 1989.

Arom, K. V., et al., "Mini–Sternotomy for Coronary Artery Bypass Grafting," The Annals of Thoracic Surgery 1996; 61:1271–2.

Arom, K. V., et al., "Mini–Sternotomy for Coronary Artery Bypass Grafting," The Annals of Thoracic Surgery 1996; 62:1884–85.

Bedellino, M.M., et al., "*The Cardiac Rag—Simple Exposure of the Heart,*" Texas Heart Institute Journal, vol. 15, No. 2, 1988, 134–35.

Beg, R.A., et al., "*Internal Mammary Retractor,*" Ann Thorac, Surg., vol. 39, No. 1, pp. 286–287, Jan. 1985.

Bonatti, J., et al., "*A Single Coronary Artery Bypass Grafting—A Comparison Between Minimally Invasive Off Pump Techniques and Conventional Procedures,*" European Journal of Cardio–Thoracic Surgery, 14 (Supp. I) (1998) S7–S12.

British Heart Journal, "Coronary Surgery Without Cardiopulmonary Bypass," pp. 203–205, 1995.

Bugge, M., "*A New Internal Mammary Artery Retractor,*" Thorac. Cardiovasc Surgeon 38, pp. 316–317 (1990).

Calafiore, A. M., et al., "*Minimally Invasive Coronary Artery Bypass Grafting,*" The Annals of Thoracic Surgery, 62:1545–8, 1996.

Campalani et al., "A New Self–Retaining Internal mammary Artery Retractor." J. Cardiovas. Surg., vol. 28. (1987).

Cartier, R, MD., "*Triple Coronary Artery Revascularization on the Stabilized Beating Heart: Initial Experience,*" Montreal Heart Institute, CJS, vol. 41, No. 4, pp. 283–288, Aug. 1998.

Chaux, A. and C. Blanche, "*A New Concept in Sternal Retraction: Applications for Internal Mammary Artery Dissection and Valve Replacement Surgery,*" Ann. Thorac. Surg. 42, pp. 473–474, Oct. 1986.

Cooley, D. A., "*Limited Access Myocardial Revascularization,*" Texas Heart Institute Journal, pp. 81–84, vol. 23, No. 2, 1996.

*Correspondence and Brief Communications*, Archives of Surgery—vol. 115, 1136–37, Sep. 1980.

Cremer, J, MD, "*Off–Bypass Coronary Bypass Grafting Via Minithoracotomy Using Mechanical Epicardial Stabilization,*" The Annals of Thoracic Surgery, 63:S79–83, 1997.

Delacroix–Chevalier Surgical Instruments, IMA Saving Packages Brochure.

DelRossi, A J and Lemole, GM, "*A New Retractor to Aid in Coronary Artery Surgery,*" The Annals of Thoracic Surgery, vol. 36, No. 1, 101–102, Jul. 1983.

Green, GE., "*Technique of Internal Mammary–Coronary Artery Anastomosis,*" The Journal of Cardiovascular Surgery, 78:455–79, 1979.

Groopman, J., "*Heart Surgery, Unplugged; Making the Coronary Bypass Safer, Cheaper, and Easier,*" The New Yorker, Jan. 11, 1999, pp. 43–46, 50–51.

Guzman, F. M.D., "*Transient Radial Nerve Injury Related to the Use of A Self Retraining Retractor for Internal Mammary Artery Dissection,*" J. Cardiovasc. Surg. 30, 1989, pp. 1015–1016.

Hasan, RI, et al., "*Technique of Dissecting the Internal Mammary After Using the Moussalli Bar*," European Journal of Cardiothoracic Surgery, 4:571–572, 1990.

Itoh, Toshiaki, M.D., et al., "*New Modification of a Mammary Artery Retractor*," Ann. Thorac. Surg. 9, 1994; 57:1670–1.

Japanese Journal of Thoracic Surgery, vol. 42, No. 2, 1989. Japanese Article "*Heart Retractor*".

Kazama, S. et al., "*Fabric Heart Retractor for Coronary Artery Bypass Operations*," The Annals of Thoracic Surgery, 55:1582–3, 1993.

Konishi, T. MD, et al., "*Hybrid–Type Stabilizer for Off–Pump Direct Coronary Artery Bypass Grafting*," Annals of Thoracic Surgery 66:961–2, 1998.

Lavergne, et al., "*Transcatheter Radiofrequency Ablation of Atrial Tissue Using a Suction Catheter*," PACE, vol. 12, Jan. 1989, Part II, pp. 177–186.

Matsuura, A. MD, et al., "*A New Device for Exposing the Circumflex Coronary Artery*," The Annals of Thoracic Surgery, 59:1249–50, 1995, pp. 1249–1250.

McKeown, P.P. et al., "*A Modified Sternal Retractor for Exposure of the Internal Mammary Artery*," Ann. Thorac. Surg. 32 (1981) 619.

Ochsner, JL, et al., "*Surgical Management of Diseased Intracavitary Coronary Arteries*," The Annals of Thoracic Surgery, vol. 38, No. 4, Jul., pp. 356–362, Oct. 1984.

Parsonnet, V. MD, et al., "*Graduated probes for Coronary Bypass Surgery*," The Journal of Thoracic and Cardiovascular Surgery, vol. 68, No. 3, 424–26 (Sep. 1974).

Parsonnet, V. MD, et al., "*Self—Retaining Epicardial Retractor for Aortocoronary Bypass Surgery*," The Journal of Thoracic and Cardiovascular Surgery, 629–30 1979.

Perrault, L. et al., "*Snaring of the Target Vessel in Less Invasive Bypass Operations Does Not Cause Endothelial Dysfunction*," The Society of Thoracic Surgeons, pp. 751–755, 1997.

Phillips, Steven J., M.D. et al., "*A Versatile Retractor for Use in Harvesting the Internal Mammary Artery and Performing Standard Cardiac Operations*," J. Thorac. Cardiovasc. Surg. (1989; 97:633–5).

Pilling Surgical Instruments, A Rusch International Company Brochure.

Pittman, John, M.D., et al., "*Improved Visualization of the Internal Mammary Artery with a New Retractor System*," Ann. Thorac. Surg., 1989; 48:869–70.

Robicsek, F., "*Aortic Spoon–Jaw Clamp for Aorta–Saphenous Vein Anastomosis*," Journal of Cardiac Surgery, 10:583–585, 1995.

Rousou, J. et al., "*Cardiac Retractor for Coronary Bypass Operations*," The Society of Thoracic Surgeons, pp. 52:877–78, 1991.

Roux, D. MD. et al., "*New Helper Instrument in Cardiac Surgery*," The Annals of Thoracic Surgery, 48: 595–6, 1989.

Roux, D., M.D. et al., "*Internal Mammary Artery Dissection: A Three Dimensional Sternal Retractor*," J. Cardiovasc. Surg., 1989; 30:996–7.

Stevens, et al., "*Closed Chest Coronary Artery Bypass With Cardioplegic Arrest in the Dog*," 67$^{th}$ Scientific Session, 238, I–251.

Trapp, et al., "*Placement of Coronary Artery Bypass Graft without Pump Oxygenator*," Journal of the Society of Thoracic Surgeons and The Southern Thoracic Surgeons Assn. vol. 19, No. 1, Jan. 1975.

USSC Cardiovascular Thora–Lift J, United States Surgical Corporation, Norwalk, Connecticut, Product Brochure.

Vigano, M., "*Tecnica Operatoria*," Minerva Cardioangiologica, vol. 23–N. 6–7 (1975).

Vincent, J.G., "*A Compact Single Post Internal Mammary Artery Dissection Retractor*," Eur. J. Cardio–Thor. Surg. 3 (1989) 276–277.

Westaby, S. et al., "*Less Invasive Coronary Surgery: Consensus From the Oxford Meeting*," The Annals of Thoracic Surgery, 62:924–31, 1996.

60/117,333 Looney et al. (provisional) filed on Jan. 24, 1999.

09/345,859 Looney et al. filed on Jul. 01, 1999.

09/438,670 Parsons, et al. filed on Nov. 12, 1999.

09/489,274 Brown et al. filed on Jan. 21, 2000.

C. W. Akins, et al., "*Preservation of Interventricular Septal Function in Patients Having Coronary Artery Bypass Graft Without Cardiopulmonary Bypass*," American Heart Journal, vol. 107, No. 2, Feb., 1984, pp. 304–309.

M. P. Anstadt, M.D., et al., "*Direct Mechanical Ventricular Actuation for Cardiac Arrest in Humans*," Chest, vol. 100, No. 1, Jul. 1991.

R. Archer, DO, et al., "*Coronary Artery Revascularization Without Cardiopulmonary Bypass*," Texas Heart Institute Journal, vol. 11, No. 1, Mar. 1984, pp. 52–57.

C. M. Ballantyne, M.D., et al., "*Delayed Recovery of Severally 'Stunned' Myocardium with the Support of a Left Ventricular Assist Device After Coronary Artery Bypass Graft Surgery*," Journal of the American College of Cardiology, vol. 10, No. 3, Sep. 1987, pp. 710–712.

M. Bashar Izzat, FRCS, et al., "*Cardiac Stabilizer for Minimally Invasive Direct Coronary Artery Bypass*," Elsevier Science Inc., 1997 by the Society of Thoracic Surgeons.

F. J. Benetti, et al., "*Direct Myocardial Revascularization Without Extracorporeal Circulation*," Chest, vol. 100, No. 2 Aug., 1991, pp. 312–316.

F.J. Benetti, et al., "*Direct Coronary Surgery with Saphenous Vein Bypass Without Either Cardiopulmonary Bypass or Caridac Arrest*," The Journal of Cardiovascular Surgery, vol. 26, No. 3, May–Jun., 1985, pp. 217–222.

C. Borst, et al., "*Regional Cardiac Wall Immunobilization for Open Chest and Closed Chest Coronary Artery Bypass Grafting on the Beating Heart; 'Octopus' Method*," Circulation, Oct. 15, 1995, vol. 92, No. 8, supplement 1, 1–177.

C. Borst, et al., "*Coronary Artery Bypass Grafting Without Cardiopulmonary Bypass and Without Interruption of Native Coronary Flow Using a Novel Anastomosis Site Restraining Device ("Octopus")*," J Am Coll Cardiol, May 1996, vol. 27, No. 6, pp. 1356–1364.

E. Buffolo, et al., "*Direct Myocardial Revascularization Without Cardiopulmonary Bypass*," Thoac. Cardiovasc. Surgeon, 33 (1985) pp. 26–29.

W. J. Fanning, MD., "*Reoperative Coronary Artery Bypass Grafting Without Cardiopulmonary Bypass*," The Annals of Thoracic Surgery, vol. 55, No. 2, Feb. 1993, pp. 486–489.

Favaloro, M.D., et al., "*Direct Myocardial Revascularization by Saphenous Vein Graft*," The Annals of Thoracic Surgery, vol. 10, No. 2, Aug. 1970.

J.D. Fonger, et al., "*Enhanced Preservation of Acutely Ischemic Myocardium with Transeptal Left Ventricular Assist*," The Annals of Thoracic Surgery, vol. 57, No. 3, Mar. 1994, pp. 570–575.

G. M. Gacioch, et al., "*Cardiogenic Shock Complicating Acute Myocardial Infarction: The Use of Coronary Angioplasty and the Integracion of the New Support Device into Patient Management,*" Journal of the American College of Cardiology, vol. 19, No. 3, Mar. 1, 1992.

V. I. Kolessov, M.D., "*Mammary Artery–Coronary Artery Anastomosis as Method of Treatment for Angina Pectoris,*" Thoracic and Cardiovascular Surgery, vol. 54, No. 4, Oct., 1967, pp. 535–544.

J. Y. Kresh, et al., "*Heart–Mechanical Assist Device Interaction,*" Trans. Am. Soc. Artif. Intern. Organs, vol. XXXII, 1986, pp. 437–443.

U. Lonn, M.D., et al. "*Coronary Artery Operation Supported by the Hemopump: An Experimental Study on Pigs,*" The Annals of Thoracic Surgery, vol. 58, No. 1, Jul. 1994, pp. 516–523.

M. G. McGee, et al. "*Extended Clinical Support with an Implatnable Left Ventricular Assist Device,*" Trans. Am Soc. Artif. Intern. Organs, vol. XXXV, 1989, pp. 614–616.

A. J. Pfister, et al., "*Coronary Artery Bypass Without Cardiopulmonary Bypass,*" The Annals of Thoracic Surgery, vol. 54, No. 6, Dec. 1992, pp. 1085–1092.

M. Riahi, et al., "*A Simple Technique and Device to Provide a Bloodless Operative Field in Coronary Artery Surgery Without Cross–Clamping the Aorta,*" The Journal of Thoracic and Cardiovascular Surgery, vol. 66, No. 6., Dec. 1973, pp. 974–978.

W. E. Richenbacher, M.D., et al., "*Current Status of Cardiac Surgery: A 40–Year Review,*" Journal of American College of Cardiology, vol. 14, No. 3, pp. 535–544.

M. C. Robinson, et al., "*A Minimally Invasive Surgical Method for Coronary Revascularization—Preliminary Experience in Five Patients,*" Circulation, Oct. 15, 1995, vol. 92, No. 8, 1–176.

S. A. Ruzevich et al. "*Long–Term Follow–up of Survivors of Postcardiotomy Circulatory Support,*" Trans. Am. Soc. Artif. Intern. Organs, vol. XXXIV, 1988, pp. 116–124.

K. H. Scholz, et al. "*Transfemoral Placement of the Left Ventricular Assist Device 'Hemopump' During Mechanical Resuscitation,*" Thoracic and Cardiovascular Surgeon, vol. 38 (1990) pp. 69–72.

J.L. Ankeney, M.D., "*The Use or Not to Use the Pump Oxygenator in Coronary Bypass Operations,*" The Annals of Thoracic Surgery, vol. 19, No. 1, Jan. 1975, pp. 108–109.

G. L. Zumbro, et al., "*A Prospective Evaluation of the Pulsatile Assist Device,*" The Annals of Thoracic Surgery, vol. 28, No. 2, Aug., 1979, pp. 269–273.

\* cited by examiner-

SURGICAL INSTRUMENTS FOR STABILIZING THE BEATING HEART DURING CORONARY ARTERY BYPASS GRAFT SURGERY

This application is a divisional of U.S. application Ser. No. 09/099,855, filed Jun. 18, 1998, now U.S. Pat. No. 6,050,266, which is a divisional of U.S. application Ser. No. 08/603,758 filed Feb. 20, 1996, now U.S. Pat. No. 5,894,843.

Diseases of the cardiovascular system affect millions of people each year and are a leading cause of death in the United States and throughout the world. The costs to society from such diseases is enormous both in terms of the lives lost and in terms of the cost of treating patients through surgery. A particularly prevalent form of cardiovascular disease is a reduction in the blood supply leading to the heart caused by atherosclerosis or other condition that creates a restriction in blood flow at a critical point in the cardiovascular system that supplies blood to the heart. In many cases, such a blockage or restriction in the blood flow leading to the heart can be treated by a surgical procedure known as a Coronary Artery Bypass Graft (CABG) procedure, which is more commonly known as a "heart bypass" operation. In the CABG procedure, the surgeon removes a portion of a vein from another part of the body to use as a graft and installs the graft at points which bypass the obstruction to restore normal blood flow to the heart.

Although the CABG procedure has become relatively common, the procedure itself is lengthy and traumatic and can damage the heart and cardiovascular system, the central nervous system, and the blood supply itself. In a conventional CABG procedure, the surgeon must make a long incision down the center of the chest, cut through the entire length of the sternum, perform several other procedures necessary to attach the patient to a heart-lung bypass machine, cut off the blood flow to the heart, and then stop the heart from beating in order to install the graft. The lengthy surgical procedures are necessary, in part, to connect the patient to a cardiopulmonary bypass machine to continue the circulation of oxygenated blood to the rest of the body while the bypass graft is sewn into place.

Although several efforts have been made to make the CABG procedure less invasive and less traumatic, most techniques still require cardiac bypass and cardioplegia (stoppage of the heart). The safety and efficacy of CABG procedure could be improved if the surgeon could avoid the need to stop the heart from beating during the procedure, thereby eliminating cardiopulmonary bypass and the lengthy and traumatic surgical procedures necessary to connect the patient to a cardiopulmonary bypass machine to sustain the patient's life during the procedure. In recent years, a small number of surgeons have begun performing CABG procedures using surgical techniques especially developed so that the CABG procedure could be performed while the heart is still beating. In such procedures, there is no need for any form of cardiopulmonary bypass, no need to perform the extensive surgical procedures necessary to connect the patient to a cardiopulmonary bypass machine, and no need to stop the heart. As a result, the surgery is much less invasive and the entire procedure can typically be achieved through one or two comparatively small incisions in the chest.

Despite the advantages, the beating-heart CABG procedure is not widely practiced, in part, because of the difficulty in performing the necessary surgical procedures using conventional instruments. If specially designed instruments were available so that the CABG procedure could be performed on the beating heart, the beating-heart CABG procedure would be more widely practiced and the treatment of cardiovascular disease in a significant patient population would be improved.

As noted above, the CABG procedure requires that a connection for the flow of blood be established between two points to "bypass" a diseased area and to restore blood flow to the heart. This procedure is known as an "anastomosis." Typically, one end of the by-pass graft is sewn to a source artery with an unobstructed blood flow, such as the left internal mammary artery (LIMA), while the other end of the graft is sewn to a target coronary artery, such as the left anterior descending (LAD) artery, that provides blood flow to the main muscles of the heart. Because the beating-heart CABG procedure is performed while the heart muscle is continuing to contract and pump blood, the anastomosis is difficult to perform because the heart continues to move and to attempt to pump blood while the surgeon is sewing the graft in place. The surgical procedure necessary to install the graft in the beating-heart CABG procedure requires placing a series of sutures through several extremely small vessels that continue to move during the procedure. Moreover, the sutures must be carefully placed so that the graft is firmly attached and does not leak when blood flow through the graft is established. It is also important that the procedure be performed rapidly because the blood flow through the target coronary artery is interrupted or reduced during the procedure to allow the graft to be installed without excessive blood loss. Also, the working space and visual access are limited because the surgeon may be working through a small incision in the chest or may be viewing the procedure on a video monitor if the site of the surgery is viewed via a surgical scope.

A current practice is for the surgeon to place sutures through the heart tissue and, by exerting opposing tension on the sutures, stretch the tissue surrounding the anastomosis to partially reduce the motion of the heart while the graft is installed. This approach is far from ideal. Alternatively, a suction device may be attached to the surface of the heart to fix the motion of the outer layer of surface tissue. In such cases, a suction device, typically having several ports incorporated into an instrument, may be attached to the heart to apply a negative pressure to the surface tissue. The negative pressure essentially attaches the surface tissue to the apparatus thereby fixing the position of a portion of the surface of the heart. Such devices are described in U.S. Pat. No. 5,727,569.

While the negative pressure approach may be effective in fixing a portion of the surface tissue of the heart, the negative pressure applied to cardiac tissue can result in temporary hematomas at the site where the suction ports attach to the tissue. Also, the exterior cardiac tissue is fixed in a configuration defined by the shape of the instrument and the orientation of the suction ports. While the heart continues to beat, the heart muscles are contracting to pump blood, which results in the muscles exerting a force directed away from the exterior tissue fixed by suction.

The beating-heart CABG procedure could be greatly improved if the heart could be stabilized during the procedure such that the motion of the heart, particularly at the site of the anastomosis, is minimized even though the heart continues to beat. If effective means for stabilizing the beating heart were available, the beating heart CABG procedure could be performed more easily, more rapidly, more safely, and with less trauma to the patient.

SUMMARY OF INVENTION

The advantages provided to a surgeon by the instruments and techniques of the invention allow the beating heart CABG procedure to be performed more rapidly, with less trauma to the patient, and without CPB or cardioplegia. This invention provides an alternative approach to the suction apparatus by providing devices and methods for stabilizing the motion of the heart using mechanical instruments specially designed to apply a stabilizing force to the heart to minimize the motion of the beating heart during a surgical procedure. The invention enables a surgeon to readily and rapidly perform a beating-heart CABG procedure without the need for cardioplegia or cardiopulmonary bypass. In particular, the methods and devices described here enable the surgeon to stabilize the heart such that an anastomosis can be more readily accomplished by enabling the surgeon to attach the graft to a target coronary artery whose motion is minimized for the duration of the surgical procedure.

Pursuant to the invention, a stabilizing device is introduced through a suitable opening in the chest to provide access to the beating heart. By contacting the heart with the stabilizing means of this invention and by exerting a stabilizing force on the heart, the motion of the heart caused by the contraction of the heart muscles is effectively eliminated such that movement of the target artery at the site of the surgery is minimized. The remainder of the heart may be allowed to contract normally or may have additional devices in place to support the heart or to restrain its motion. An important advantage of this invention is derived from the discovery that an effective procedure can be followed using the devices of the invention to provide an advantageous technique for stabilizing the beating heart. The procedure requires exerting a stabilizing force on the beating heart using devices constructed as described herein. Typically, in separate steps, the surgeon contacts the heart with the stabilizing means, assesses the degree of movement at the site of the surgery and positions the stabilizing means proximate to the target coronary artery. With the stabilizing means in place, the surgeon applies a stabilizing force to the stabilizing means by applying a force such that the portion of the instrument in contact with the surface of the heart displaces the surface of the heart a sufficient distance that the contraction of the heart does not cause either vertical or horizontal motion at the surgery site. The stabilizing force is applied by the stabilizing means of the invention and comprised of exerting a mechanical force onto the beating heart at the location of the target coronary artery. Thus, an important aspect of this invention is the discovery that the beating heart may be effectively stabilized for the purpose of a surgical procedure by using a specially designed instrument as described herein to exert a mechanical stabilizing force on the exterior of the heart proximate to the site of the surgery.

By fixing the position of the stabilizing means in a configuration where the motion of the beating heart is effectively eliminated, the surgeon maintains the stabilizing force on the beating heart for the duration of the procedure. To fix the position of the stabilizing means, the means may be attached to a retractor used to separate the ribs or to another fixed support. Alternatively, the stabilizing means may be attached to a semi-rigid conformable arm which is rendered rigid mechanically, chemically, or by human intervention. In certain preferred embodiments, the stabilizing means has an adjustable shaft means which may be oriented in several directions and has a fixture adapted to be attached to a retractor. In a preferred technique of the invention, the surgeon first performs a thoracotomy, retracts the ribs using a retractor which is locked in an open position providing access to the beating heart. The surgeon then contacts the surface of the heart with the stabilizing means at a point proximate to the target coronary artery, and exerts a stabilizing force on the stabilizing means until the site of the surgery is substantially motionless. At this point, the adjustable shaft means is positioned and fixed in place by attachment to the retractor thereby rendering the target coronary artery substantially motionless for the duration of the procedure.

DESCRIPTION OF THE FIGURES

FIG. 1 also shows the contact members attached to a shaft means which may be adjustable in several directions and which may be attached to a retractor or other fixed support structure.

FIG. 5A is a partial side view of the system of FIG. 5.

DETAILED DESCRIPTION OF THE INVENTION

Figure 1:
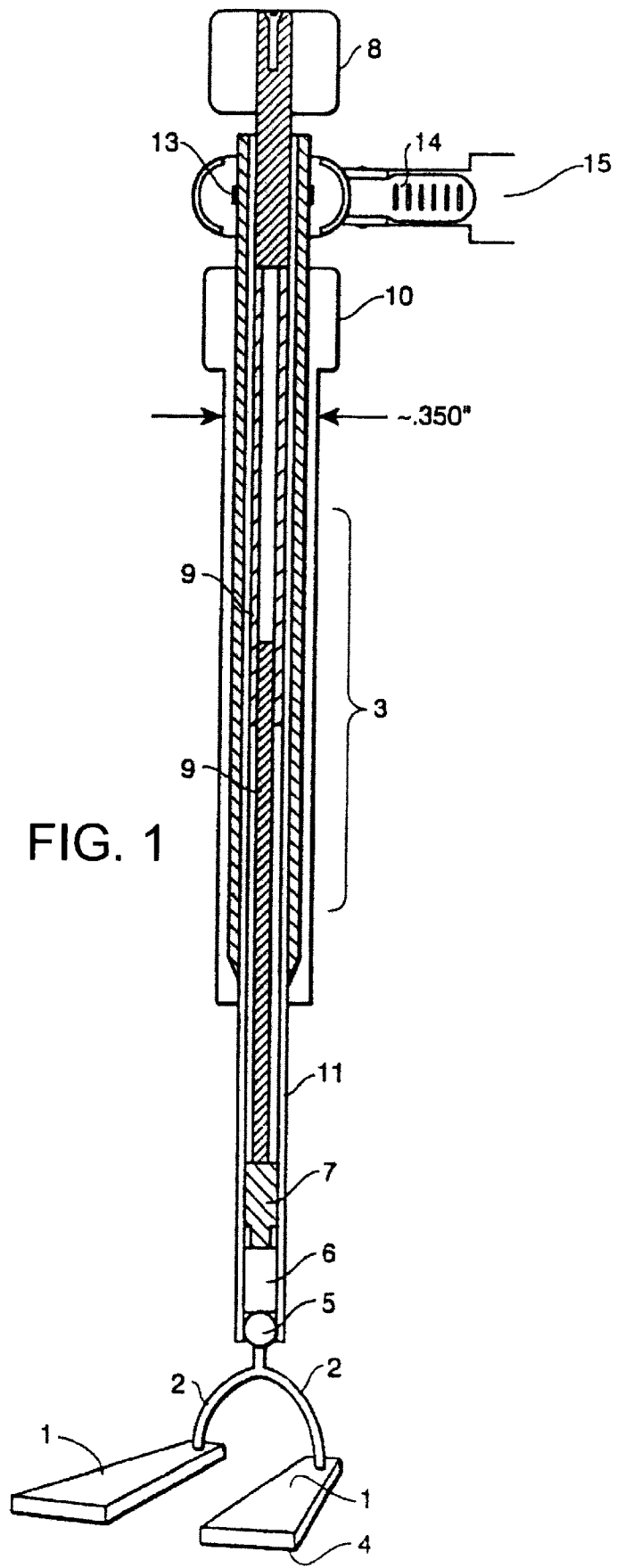
FIG. 1 is a means for stabilizing the beating heart having a pair of substantially planar contact members which engage the heart on either side of a target coronary artery to which a bypass graft is sewn.
Figure 1A:
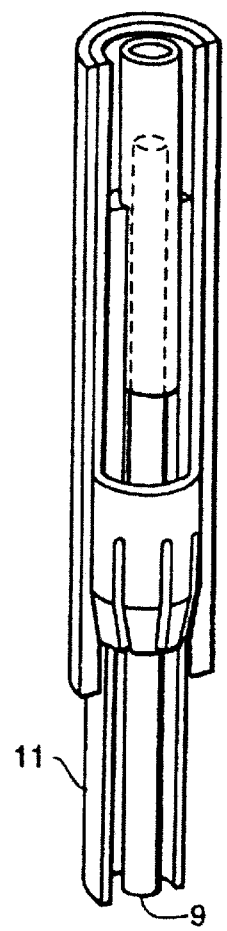
FIG. 1A is detail of the shaft means and the structure of the adjustable positioning mechanisms.

The present invention includes surgical instruments for stabilizing the beating heart and methods for their use. The means for stabilizing the beating heart comprised several alternative structures which engage the surface of the heart to stabilize the beating heart during coronary surgery. The instruments provide the capability to exert and maintain a stabilizing force on the heart by contacting the heart with the stabilizing means and by fixing the position of the stabilizing means throughout the duration of a surgical procedure.

The instruments and methods of the invention are preferably used for stabilization of the beating heart during a minimally invasive coronary artery bypass graft (CABG) operation which has been specially developed to facilitate placement of a bypass graft without cardioplegia or cardiopulmonary bypass. Although the means for stabilizing the beating heart can be applied in different surgical contexts, the devices described herein are most advantageously employed in a CABG procedure wherein only one or two incisions are placed in the chest. The structure of the stabilizing means may be described by several structural embodiments which stabilize the beating heart while the minimally invasive surgical procedure is performed. The stabilizer means may also advantageously function in a multiple component system containing a retractor, an occluder, a surgical blower or suction device, an apparatus for holding the source artery, such as a LIMA holder, or other like devices to enable a surgeon to more efficiently complete the anastomosis. While the devices disclosed herein each use mechanical means to stabilize the beating heart, certain embodiments are designed to operate on the entire heart while others have more localized effect and may be applied to the area immediately proximate to a structure such as the target artery of the anastomosis. In each instance, the beating heart is effectively stabilized at the area where a surgical procedure is to be performed. Surgical access to the beating heart may be achieved by several conventional cardiac surgical procedures which have been developed for traditional bypass surgery. The surgeon may obtain the advantages provided by the invention in any procedure where the bypass is achieved on the beating heart. When access to the beating heart is achieved by a sternotomy, the length of the sternum is separated to expose the surface of the heart. Preferably, the surgeon takes additional measures to restrict the movement at the entire heart within the chest cavity. For example, an inflatable cushion with straps or laces may be inserted beneath or surrounding the heart. Additionally, when the pericardium is available, the pericardium may be incised and used to position the beating heart. When the pericardium is available, the surgeon can use the pericardium to raise and rotate the beating heart within the chest cavity and maintain the position by suturing the pericardium to the periphery of the incision.

In the preferred embodiment, minimally invasive access to the beating heart is achieved by a thoracotomy, which is usually created in the left side of the chest by a vertical incision between the ribs, insertion of a retractor between the ribs, followed by spreading of the ribs and securing the retractor in an open position to provide access to the source artery and the target coronary artery. The use of the pericardium to position the beating heart as described above is particularly advantageous when the less invasive thoracotomy is used to provide access to the heart. An incision is created in the pericardium which is then sutured to the periphery of the thoracotomy. In this configuration, the pericardium acts as a restraining sac to keep the beating heart in a desired orientation to achieve the anastomosis. The means for stabilizing the beating heart is introduced through the opening created by the thoracotomy and is brought into contact with the heart. The surgeon applies a stabilizing force to the heart via the stabilizing means which may then be fixed in place by attachment to a fixed support. When the rib retractor or platform is fixed in an open position to expose the heart, the retractor platform may also provide an advantageous stable support structure to which the stabilizing means may be affixed. When the position of the stabilizing means is fixed by attachment to a stable support or to the retractor platform, the stabilizing force is maintained for the duration of the procedure.

Although the particular source and target artery of the anastomosis are determined clinically, a common minimally invasive bypass procedure on the beating heart comprises an anastomosis which forms a connection between the left internal mammary artery (LIMA) as the source artery and the left anterior descending artery (LAD) as the target artery. The LIMA to LAD anastomosis is used as an example herein but it is readily appreciated that the techniques and instruments described herein may be applied to other procedures depending on the clinical diagnosis. To complete the anastomosis, the surgeon must dissect a portion of the LIMA by separating it from the internal chest cavity. Once dissection of the LIMA is achieved, the surgeon may attach the dissected LIMA to the target cardiac artery, in this example, the LAD. In this example, the stabilizing means of this invention would be used to stabilize the beating heart during at least the portion of the procedure during which the surgeon completes the anastomosis to the LAD.

The structure of the portion of the stabilizing means which contacts the heart includes an inflatable member, a platform which may be substantially planar or which may be contoured to fit conformingly on the surface of the heart, one or more contact members which exert a stabilizing force on the heart proximate to the site of the anastomosis, a pair of contact members which may be plates or rectangular members which are placed on either side of the target coronary artery at the site of the anastomosis and which may have a friction or tissue spreading means associated therewith. The stabilizing means may also include a shaft means having several alternative embodiments to facilitate adjusting the position and orientation of the instrument. For example, the shaft means may have an adjustable length and the axis of the shaft means may have at least one ball joint disposed within its length such that the orientation of the shaft means relative to another structure such as the contact members on the retractor may be continuously varied. As is apparent from the description of the several embodiments, each of the individual embodiments described and illustrated herein has discrete components and features which may be readily separated from or combined with the features of any of the other several embodiments without departing from the scope of the invention.

Referring to FIG. 1, a stabilizing means comprises one or more, and preferably two, contact members 1, which are attached to a rigid, or semi-rigid connecting shaft 2 which is in turn connected to shaft means 3. The contact members 1 may be substantially planar or may be slightly curved to conform to the shape of the heart. The contact members 1 may have any of several alternate shapes including cylindrical members formed into a U-shape or may comprise a pair of substantially parallel members spaced apart in a parallel configuration such that a target artery can be positioned between the contact members. The shape of the contact members may be varied depending on the clinical assessment by the surgeon, the design of the other features of the stabilizing means, or the design of other instruments used to complete the anastomosis. In some embodiments, as described herein, the contact members 1 may have apertures, openings or attachments to facilitate connection with sutures or other devices to achieve the requisite stabilization. In a preferred embodiment, a pair of substantially planar rectangular contact members 1 are attached at one end to a continuous connecting shaft 2 and are oriented in a substantially parallel fashion such that a target cardiac artery is positioned therebetween and passes along the length of the contact members 1 when the stabilizing means engages the heart. See FIGS. 9A–C. While the contact members 1 may each be connected to the connecting shaft 2 at one end, with the connecting shaft 2 operably attached to shaft means 3, the configuration of the connecting shaft 2 relative to the contact members 1 may be altered depending on the configuration of the contact members 1 and the clinical aspects of the procedure. For example, the connecting shaft may be continuous to connect with the contact members 1 without touching the artery or may include an additional member which may be operated to contact the target artery positioned between the contact members 1, see FIG. 8, to occlude the passage of blood through the target artery. The contact members 1, connecting shaft 2 and shaft means 3 may be composed of any non-toxic material such as a biocompatible plastic or stainless steel, having sufficient tensile strength to withstand a stabilizing force exerted on the heart via manipulation of the shaft means 3 to cause the contact members 1 to exert a stabilizing force on the beating heart.

The shaft means 3 may be a simple rigid post or may comprise a multi-component system designed to be adjustable in length and orientation at at least one point along its length. Thus, the length of the shaft means 3 and the orientation of the contact members 1 at the distal (lower) end of the shaft means 3 can be altered by the surgeon. Preferably, the length and orientation at the shaft means 3 relative to the contact members 1 can be adjusted by controls located at the proximate (upper) end of shaft means 3. This design provides the advantage that the surgeon can introduce the stabilizing means to the beating heart by placing the contact members 1 on the surface of the heart, exerting a stabilizing force, and then locking the contact members 1 in place relative to the shaft means 3. Furthermore, the surgeon may then lock the shaft means 3 into a fixed position by attachment to a stable support such as the retractor, thereby maintaining the stabilizing force for the duration of the procedure. In one embodiment, the shaft means 3 has a housing 11 whose overall length is adjustable by a telescoping release of additional housing 11 length operated by an annular thumbscrew 10 which tightens about the housing 11. The position and orientation of the contact members 1 relative to the shaft means 3 is adjustable by virtue of a locking ball joint 5 which is interposed between the connecting shaft 2 and which is located at the distal end of shaft means 3. The locking ball joint 5 allows the position of the shaft means 3 to be positioned with three degrees of freedom relative to the contact members 1.

Referring again to FIG. 1, a locking ball joint 5 is provided by including a block 6 within the shaft means 3 which conformingly contacts the ball joint 5 and fixes the position of the ball joint 5. Block 6 is compressed against ball joint 5 when a threaded push block 7 connected to a long allen 9 is actuated by means such as a thumbscrew 8 at the upper end of the shaft means 3. In operation, a rotation of the top thumbscrew 8 loosens the lower ball joint 5 to allow continuous positioning of the shaft means 3 relative to the contact members 1, and a counterrotation locks the ball joint 5 into place, fixing the position of the contact members 1 relative to shaft means 3.

The upper end of shaft means 3 may also have associated therewith an upper ball joint 13 such that the shaft means 3 can be oriented with three degrees of freedom relative to a fixed support such as a retractor. The position and orientation of the shaft means 3 may thus be fixed relative to the stable support by a locking latch 14 or other conventional mechanism which prevents movement of the upper ball joint. Either the shaft means 3 or the retractor may contain the locking latch 14 surrounding the upper ball joint 13 or any like fixture to firmly attach the shaft means 3 to a stable support, e.g., an anchor portion 15 extending from the retractor (not shown).

Figure 1B:
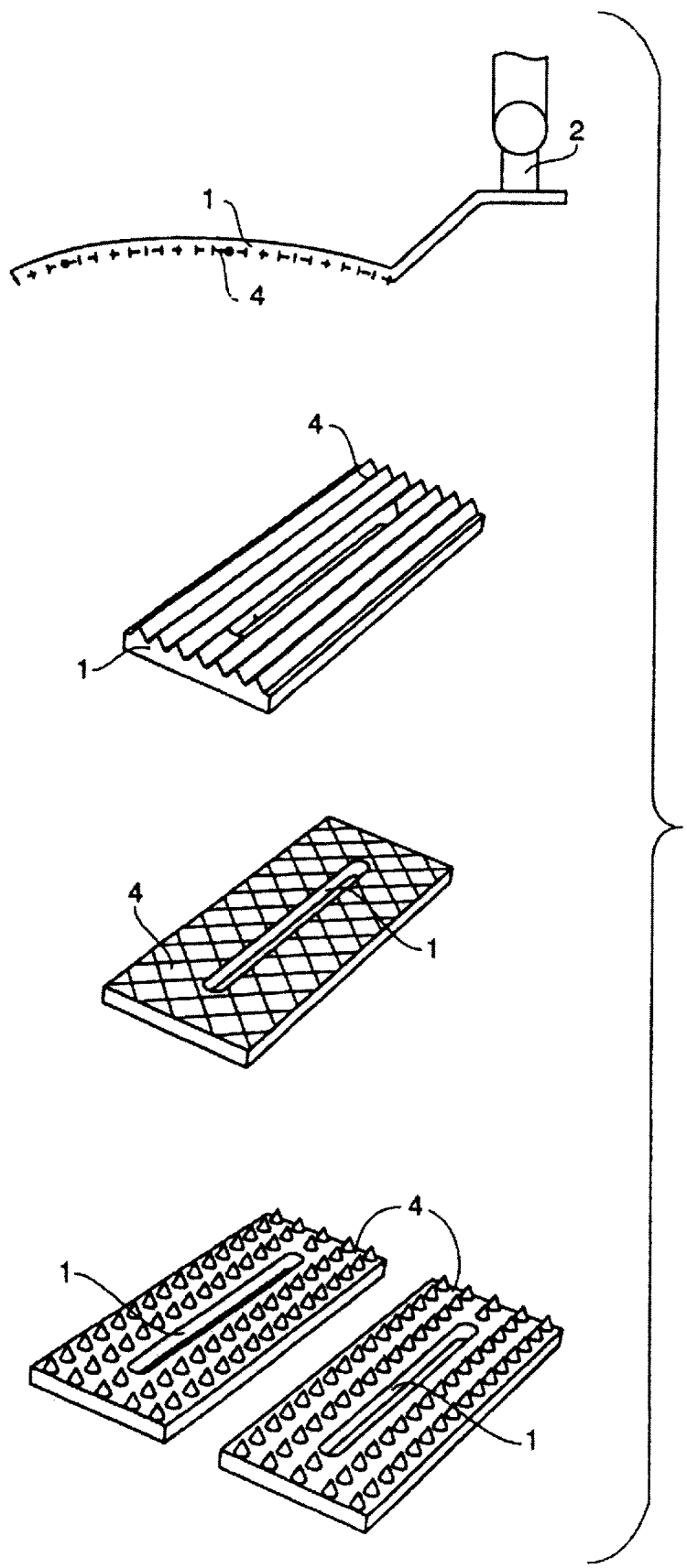
FIG. 1B is a contact member having a friction means which is preferably affixed to the bottom surface of the contact member.

Referring to FIG. 1B, the contact members 1 preferably have friction means 4 associated with their bottom surfaces such that the contact members 1 more securely engage the beating heart when a stabilizing force is exerted on the shaft means 3. The friction means 4 preferably comprises a textured surface covering the bottom surface of the contact member 1, and may be comprised of several bio-compatible substances such as a textured rubber, textured or ridged aluminum, stainless steel or the like.

As noted above, at the upper end of the shaft means 3, the shaft means 3 may be attached to a fixed support, such as by anchor portion 15, which may be any surface or structure which does not move with the beating heart. For example, the shaft means 3 may be attached to a fixture on the retractor system used to spread the ribs for access to the heart or may be attached to a fixed structure such as the surgical table or associate aperture which is not connected to the patient. In a preferred embodiment, the shaft means 3 is directly attached to a component of the retractor system which is designed to receive the shaft means 3 and to maintain the position and orientation of the shaft means 3 during the procedure.

The shaft means 3 may also be attached to, or comprise, a conformable arm which is used to position the stabilizing means against the heart and then to lock the stabilizing means in place once a stabilizing force has been exerted. The conformable arm is flexible and lockable and may have several configurations including a plurality of links, segments, or universal joints in serial configuration and having a cable fixture passed through the interior of the links which cause the entire conformable arm to become rigid by tightening the cable fixture. Also, the conformable arm may comprise a synthetic gel or polymer contained within a conformable cylindrical housing and which becomes rigid upon exposure to light or heat, such as the commercially available Dymax 183-M. Where the shaft means 3 further comprises; and the conformable arm, the conformable arm may be attached directly to the connecting shaft 2 or the contact members 1.

Figure 2B:
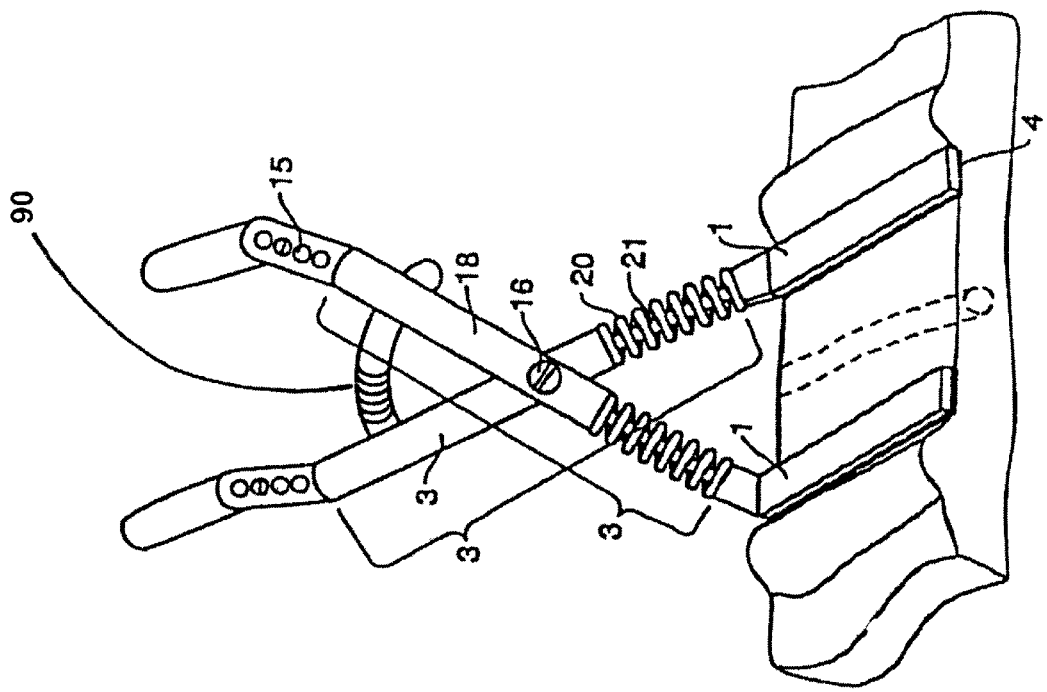
FIGS. 2A and 2B show an alternate embodiment of a stabilizing means having a single shaft means associated with each contact member and where the shaft means are interconnected and can be moved independently about a pivot such that the contact members spread the surface tissue of the heart proximate to the target coronary artery to increase exposure of the target artery at the site of the anastomosis.
Figure 2A:
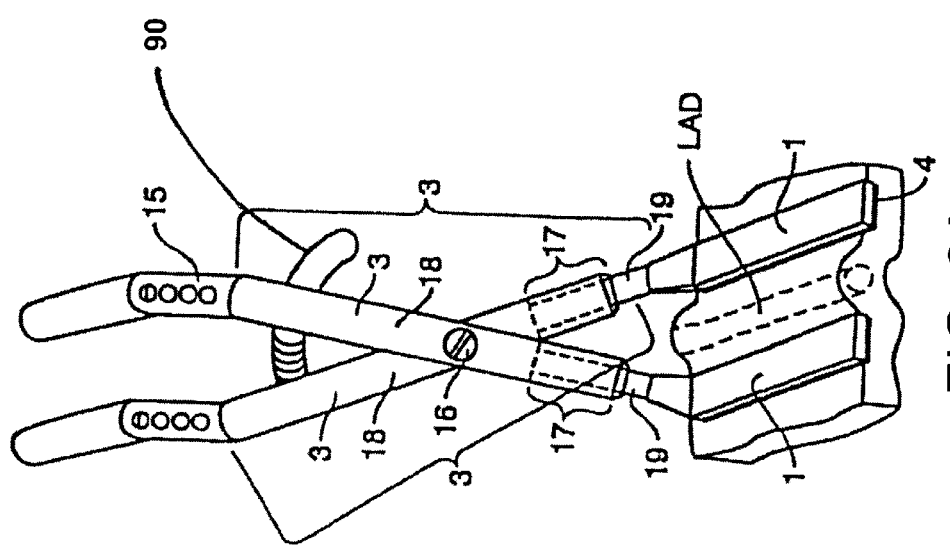

Referring to FIG. 2, the stabilizer means may also comprise a single shaft means 3 connected to each contact member 1. In a preferred embodiment, the shaft means 3 are interconnected at an intermediate pivot point 16 which permits the contact members 1 to be continuously positioned in parallel fashion relative to one another. The proximate (upper) portion of the individual shaft means 3 may have grips adapted to be grasped by the hand or may have an anchor portion 15 for attachment to a retractor or other fixed support. As with the other embodiments described herein, the length of the shaft means 3 may be adjustable by a conventional telescope configuration. In such a configuration, a first shaft 18 has a partially hollow segment 17 adapted to receive the complimentary portion of the second shaft 19. Either first 18 or second 19 shafts may be connected to the contact members 1 and may each have a conventional locking mechanism (not shown). The shaft means may also have a tensioning spring mechanism having an axis 21 which is displaced between a portion of the shaft means 3 affixed to the contact members 1 and the remainder of the shaft means 3. In this configuration, the contact members 1 remain tensioned against the heart proximate to the anastomosis site when the proximal end of the shaft means 3 is affixed to a stable support. The shaft means may also comprise an interlocking mechanism 90 to fix the position of a single shaft 18 relative to the other. This embodiment also preferably has a friction means 4 as described above attached to each contact member 1. An additional advantage of this embodiment is derived from the capability to move the contact members 1 apart from one another in a parallel configuration. Thus, the contact members 1 can first be positioned to engage the surface of the heart tissue, followed by the application of a stabilizing force in combination with spreading of the proximate (upper) end of the shaft means 3. Application of a stabilizing force causes the tissue on either side of the target artery to be stabilized. By coincidentally spreading the proximate portion of the shaft means 3, the tissue engaged by the contact members 1 is stretched to provide stabilization and improved exposure of the target coronary artery.

Figure 3:
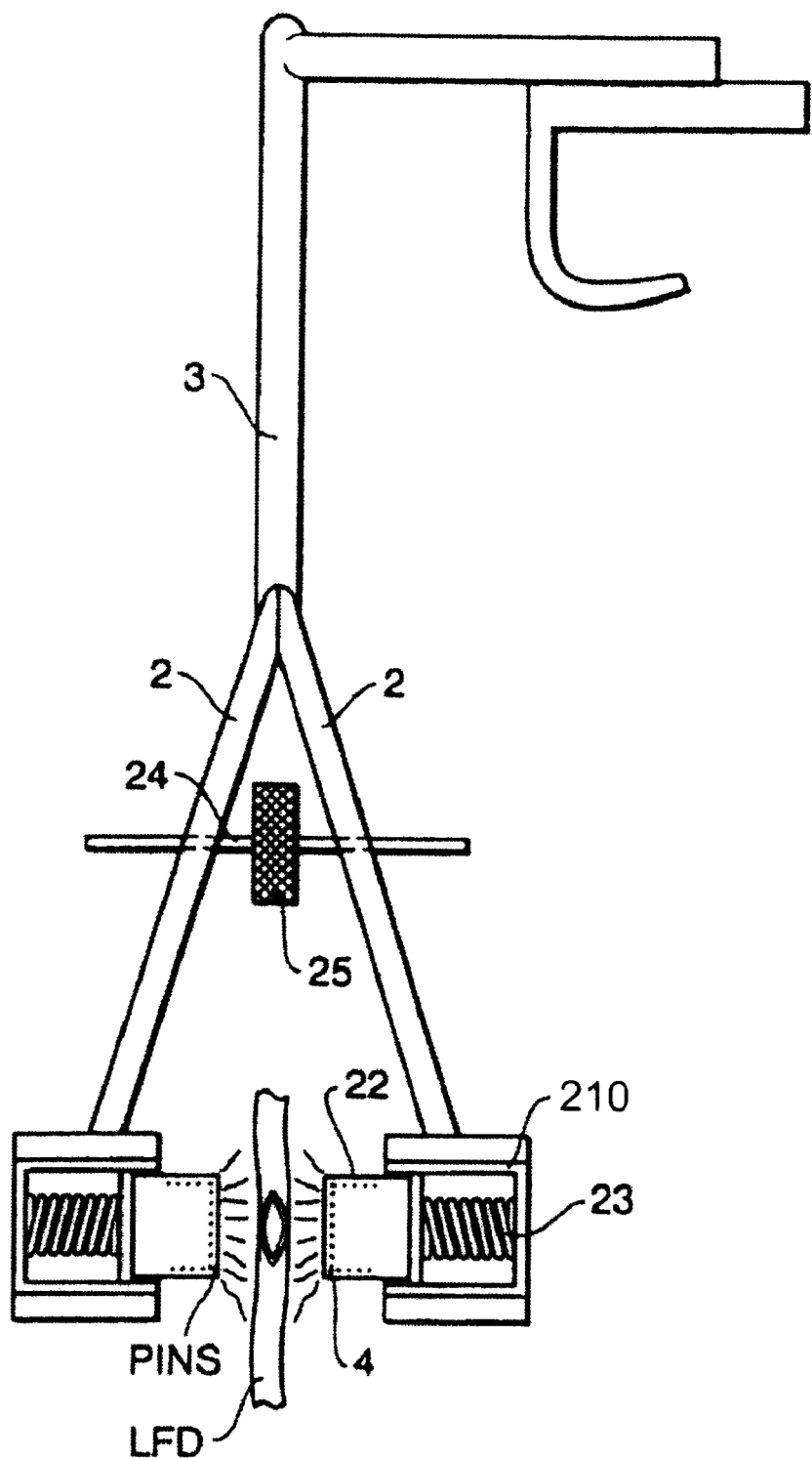
FIG. 3 is a means for stabilizing the beating heart having a pair of contact members which additionally comprise a spring-tensioned frame having an extension that engages and spreads the tissue at the site of the surgery to better expose the coronary artery.

Referring to FIG. 3, the contact members 1 may be further comprised of a spring-tensioned frame 210 having a movable frame extension 22 which may have pins or an associated friction means 4 to engage the tissue proximate to the target artery. The movement of the frame extension 22 is tensioned by a spring means 23 which draws the frame extension 22 toward the contact member 1 after the frame extension 22 has been manually positioned to engage the tissue. The use of this embodiment of the invention is the same as is described for the other embodiments herein, with the frame extension 22 providing improved exposure of the target artery. As with the other embodiments of the invention disclosed herein, the contact members 1 may be attached at one end by a connecting shaft 2 which is attached to a shaft means 3 as described above. The connecting shafts 2 may also be positioned relative to one another by a conventional threaded post 24 with a positioning thumbscrew 25.

Figure 4:
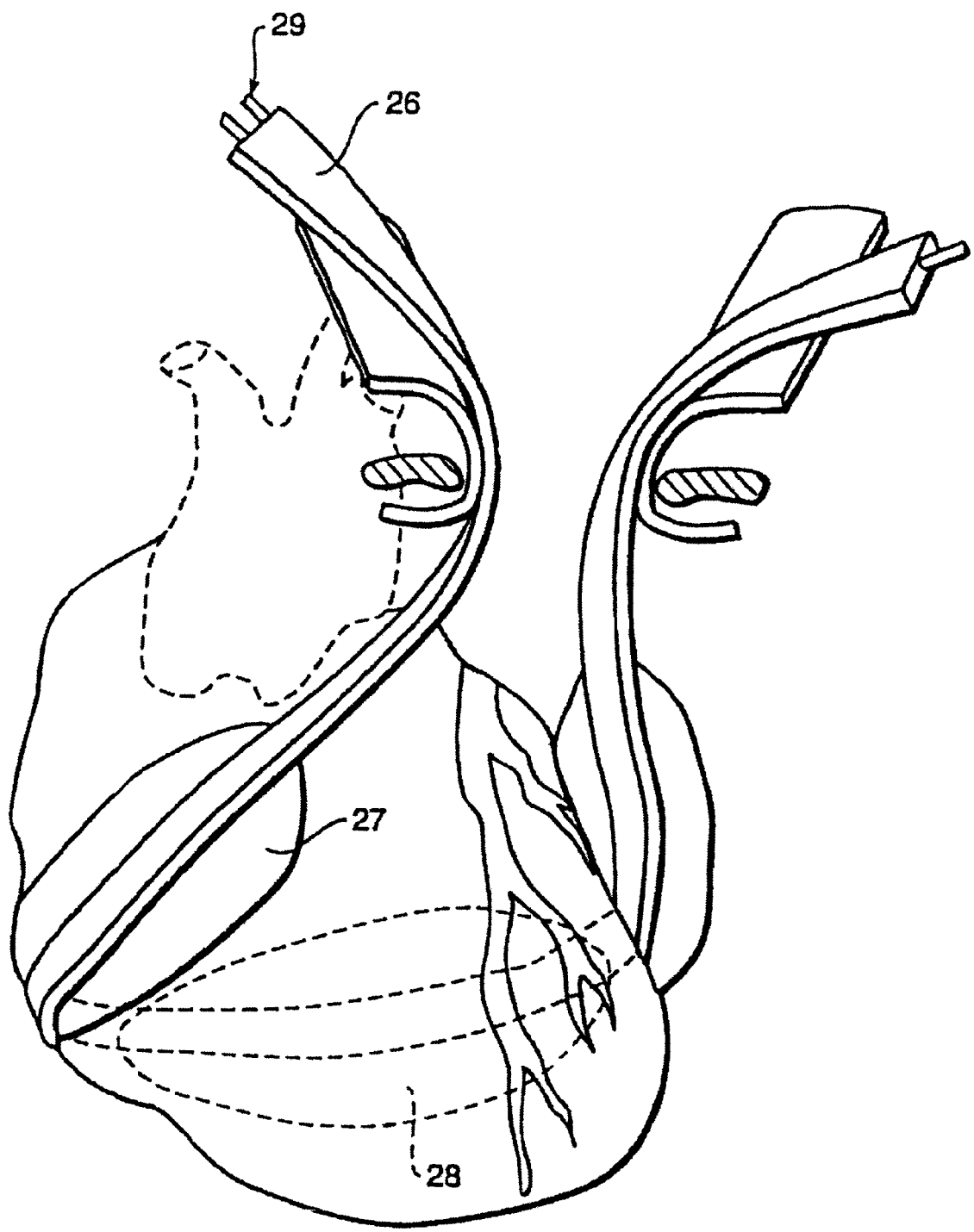
FIG. 4 is an inflatable means for stabilizing the beating heart having a sheath member with several pliable support attachments associated therewith which may include inflatable members which are positioned at one or several locations surrounding the heart and may have a lumen disposed within the sheath member for the introduction of air or a biocompatible fluid.

FIG. 4 shows an embodiment of a stabilizing means comprising an elongated sheath member 26 which wraps around the heart in a strap-like fashion to restrict the motion of the heart. This embodiment is particularly useful when access to the beating heart is provided by a sternotomy. The sheath member 26 is positioned to surround the heart and can be manipulated so that each end of the sheath member 26 extends out of the chest cavity through the sternotomy. If desired, at least one end of each sheath member 26 is attached to the retractor to secure the position of the sheath member 26. The sheath member 26 may have a plurality of support attachments 27 which engage the exterior of the heart to hold it in place. At the point where the support attachments 27 contact the surface of the heart, the support attachments 27 may have friction means 4 attached to the surfaces which are in direct contact with the heart. The support attachments 27 may have or comprise inflatable members 28 which cushion the heart against the sheath member 26, and absorb the motion of the heart while it is stabilized. Where the sheath member 26 has a plurality of inflatable members 28, the sheath member 26 preferably further comprises at least one lumen 29 for introduction of air or a biocompatible fluid to the inflatable members 28, which may be inflated separately or simultaneously. In the former instance, a separate lumen 29 is provided for each inflatable member 28. The insertion of the sheath member 26 into the chest cavity should be performed while the inflatable members 28 are deflated and is achieved manually or by a conventional guide and/or guidewire. Each of the support attachments 27 may be permanently attached to the sheath member 26 or may slide along the length of the sheath member 26. Alternatively, alone or in combination with at least one other inflatable member 28, an inflatable member 28 may be positioned immediately proximate to the target coronary artery to achieve a more localized stabilization. The inflatable member 28 is positioned to lie next to, or may surround, the target coronary artery and may have openings or apertures placed in the body of the member through which surgical procedures are performed.

Figure 5:
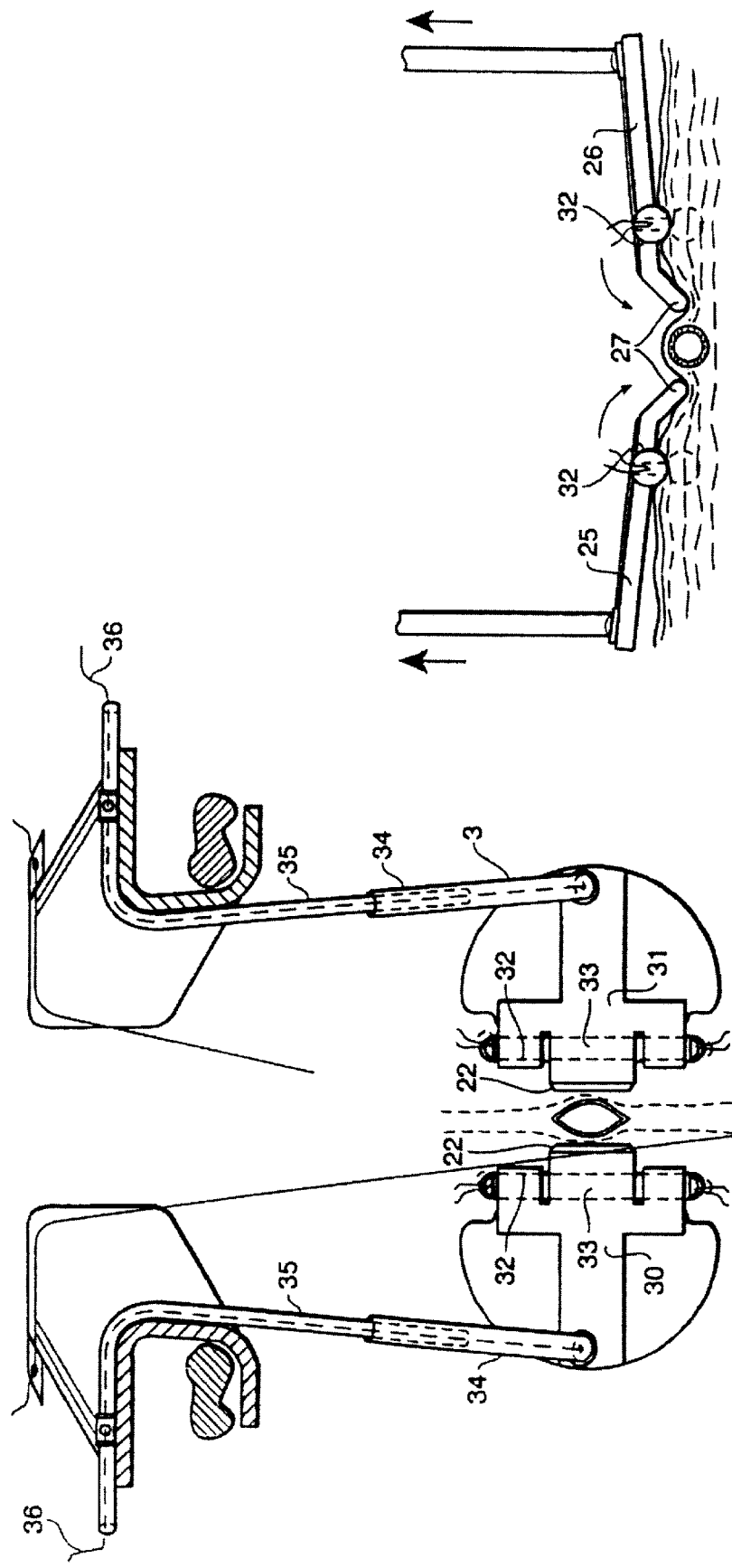
FIG. 5 is a means for stabilizing the beating heart comprising a system which incorporates the retractor which spreads the ribs to provide surgical access to the heart. The stabilizing means comprises a pair of stabilizing plates which may be used together with a lever device to improve exposure of the target coronary artery.

Referring to FIG. 5, the stabilizer means may comprise at least one stabilizer plate which is attached to a stable support and which may be used with a lever member for improving exposure at the target artery while the anastomosis is completed. In this embodiment, the means for stabilizing the beating heart comprises a left and right stabilizing plate 30, 31 which are oriented to exert a downward force on the tissue at either side of the target artery at the anastomosis site and which may be substantially planar or may be curved to conform to the surface of the heart. One or both of the stabilizing plates 30, 31 may have an edge 27 deflected downward along its length so that the edge 27 depresses the tissue proximate to the artery to increase the exposure of the artery during the completion of anastomosis. Preferably, the edge 27 of the stabilizing plates 30, 31 has a separate lever member 33 running substantially parallel to the artery and on both sides thereof. The top portion of each lever member 33 contacts the underside of the stabilizing plates 30, 31. In this embodiment, the lever member 33 is substantially cylindrical, traverses the stabilizing plate along its length, and is oriented to be parallel to the edge 27 of the stabilizing plate 30, 31. The lever member 33 is fixed in place, and may be affixed to the heart by a suture. In such a configuration, each of the stabilizing plates 30, 31, which is in contact with the lever member 33 along its length, contacts the heart such that the edge 27 depresses the tissue on both sides of the target coronary to restrict the movement of the beating heart. The stabilizing plates 30, 31 can be attached to one another or can move independently as desired.

Opposite the edge 27, at a point separate from the lever member 33, the stabilizing 30, 31 plate is connected to a shaft means 3 which holds the stabilizing plate 30, 31 in position and which may be manipulated relative to the lever member 33 to cause the edge 27 to engage the heart. The shaft means 3 is preferably affixed to each stabilizing plate 30, 31 at a point opposite the edge 27 and removed from the point where the lever member 33 contacts the stabilizer plate 30, 31 at a location to maximize leverage when the stabilizer plates 30, 31 are drawn upwards at the point of attachment of the shaft means 3. The shaft means 3 may be constructed as described elsewhere herein and should be of sufficient length to facilitate manipulation of the shaft means 3 by the surgeon. As noted, the shaft means may also be attached to the retractor to fix movement of the stabilizing plates 30, 31 during the procedure.

In a preferred embodiment, the length of the shaft means 3 is adjustable relative to the retractor or other stable support. For example, the shaft means 3 may be telescopic as described above or may be comprised of a hollow post 34 which receives a rigid shaft 35 which is in turn fixed to the retractor. The rigid shaft 35 may also be substantially hollow and may have a suture or other line 36 passed therethrough and which also passes through the length of the hollow post 34. In this configuration, one end of the suture or line 36 is attached to the stabilizing plate 30, 31 and the other end extends through the hollow post 34 or the rigid shaft 35 to a position where it may be manipulated by the surgeon. The position of the stabilizing plate 30, 31 may thereby be remotely actuated. By drawing tension on the suture or line 36, the stabilizing plate 30, 31 pivots about the lever member 33 and the edge 32 of the stabilizer plates 30, 31 depress the tissue on either side of the target artery.

Figure 6:
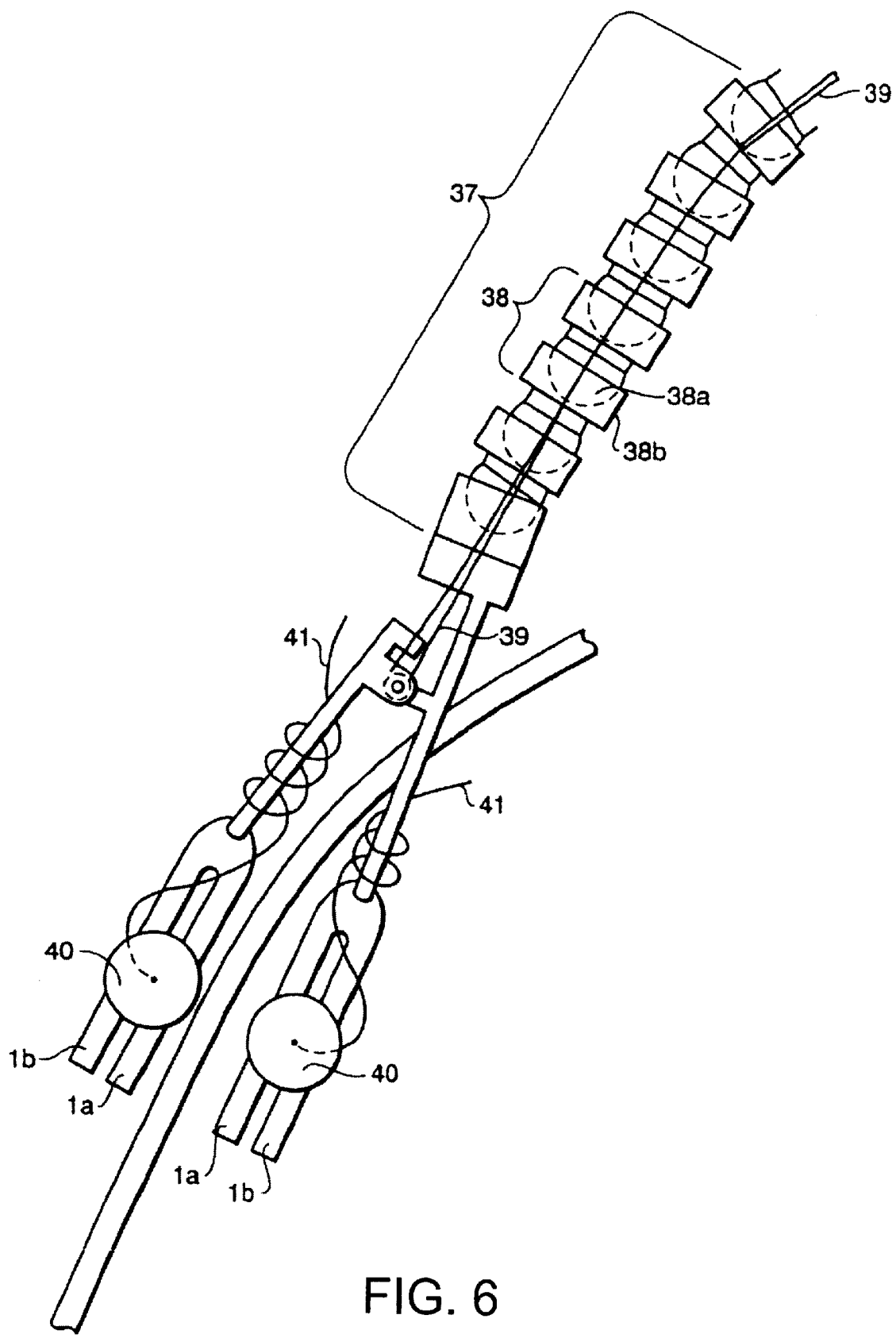
FIG. 6 is a flexible, lockable arm which allows positioning in every direction to place and orient the contact members until the requisite degree of stabilization is achieved at which point the arm having a stabilizing means is fixed in position. The flexible, lockable arm may be attached to a retractor and is caused to become rigid when the entire stabilizing means is properly positioned.

Referring to FIG. 6, this embodiment of the invention is a means for stabilizing the beating heart wherein the shaft means comprises a flexible, lockable arm 37 having a plurality of interconnecting links 38 which allow positioning of the flexible arm 37 in every direction until the desired configuration is achieved at which point the flexible arm 37 may be locked into fixed configuration by tightening a cable fixture (not shown) attached to a cable 39 running axially through the interconnecting links 38. Each interconnecting link is comprised of a ball portion 38a and a receiving portion 38b such that the ball portion 38a fits conformingly within the receiving portion 38b. The proximate (uppermost) end of the flexible, lockable arm 37 can be attached to a stable support, or to the retractor. In a preferred embodiment, the flexible, lockable arm 37 is a series of interconnecting links 38 having a cable 39 running through the center of each interconnecting link 38 such that when tension is exerted on the cable 39, the flexible, lockable arm 37 is fixed in a rigid position. FIG. 6 also shows an embodiment of the invention wherein the contact members 1 each comprise a pair of substantially parallel elements 1a, 1b which are positioned to receive a simple snap fixture 40 which is affixed to the surface of the heart. In this embodiment, the snap fixture 40 is positioned between the two parallel elements 1a, 1b of the contact member 1, in order to fix the position of the heart tissue relative to the contact members 1. As in the above embodiment, the contact members 1 are preferably oriented in a substantially parallel fashion with the target artery of the anastomosis passing therebetween. The snap fixtures 40 are affixed to the heart by a suture, wherein the suture line 41 may then also be attached to the contact member 1 via a notch, which may form a one-way locking mechanism to secure the suture line 41, or may be attached to a circular post disposed in the body of the contact member 1. The suture line 41 then may be tied through the notch or to the post in the contact member 1 to more tightly secure the heart to the contact member 1. An additional advantage of this embodiment is that the stabilizing means is actually affixed to the cardiac tissue via the suture line 41, such that when the heart is moving laterally or downward the artery being stabilized remains immobile.

Figure 7:
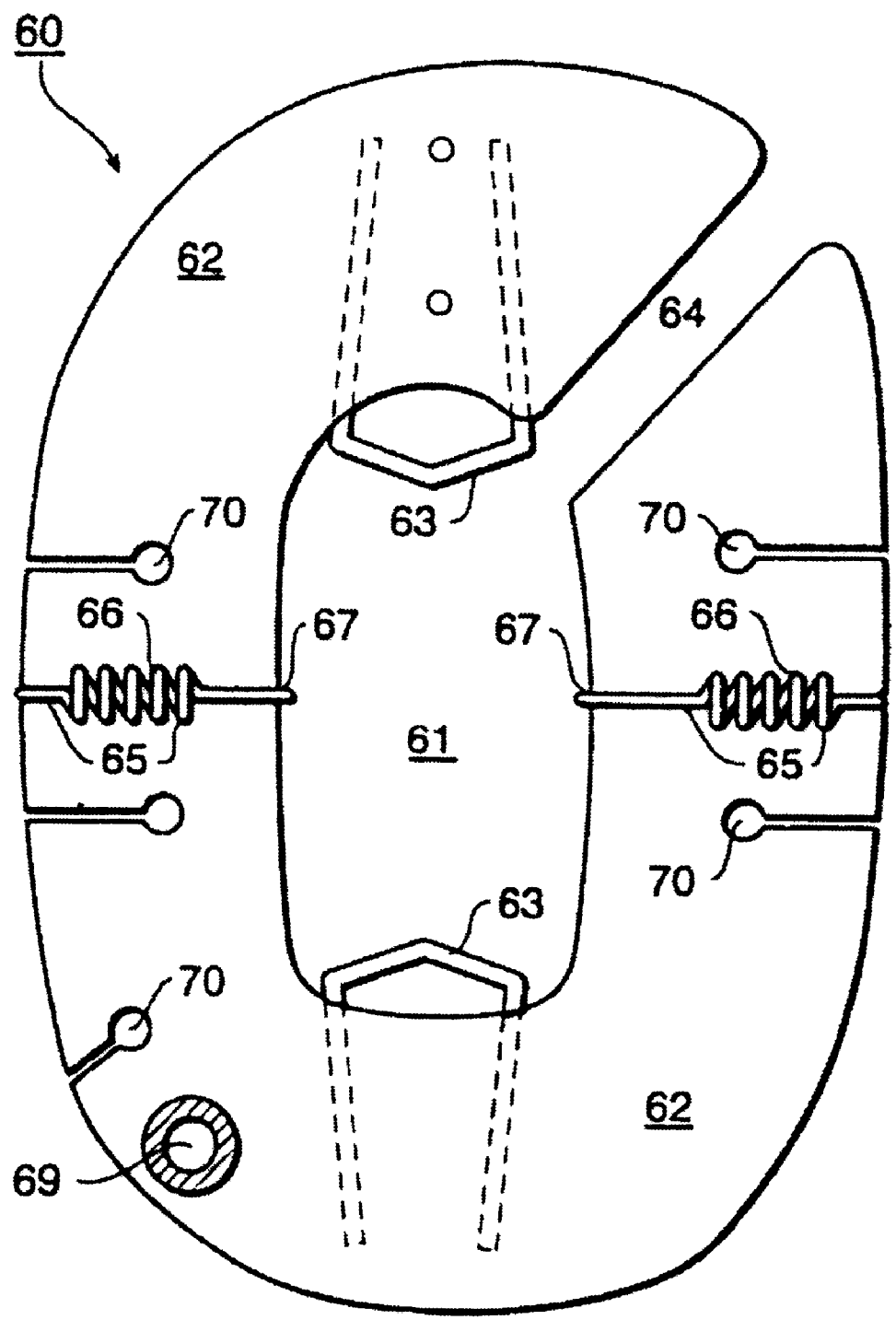
FIG. 7 is a substantially planar stabilizing platform which contacts the heart at a site proximate to and surrounding the coronary vessel. The platform may also have associated therewith at least one occluder which restricts or eliminates blood flow through an artery and an associated device for spreading the tissue proximate to the anastomosis.

Referring to FIG. 7, a stabilizing means 60 comprises a substantially planar and substantially rigid surface 62 having a centrally disposed opening 61 in which the target artery of the anastomosis is positioned longitudinally through the opening. At either or both ends of the centrally disposed opening 61, an occluder 63 extends below the surface 62 and engages the target artery to substantially reduce or eliminate the flow of blood through the artery. The occluder is a rigid member having a smooth outer surface for contacting and depressing the target artery without damaging the tissue. The planar surface 62 of the stabilizing means also has an aperture 64 comprising an opening which joins the periphery of the planar surface 62 with the centrally disposed opening 61, so that the anastomosis can be passed through the aperture 64 when the anastomosis is completed. The planar surface 62 may also provide a mounting surface for springed tissue retractors 65 comprising a coiled spring 66 attached to the planar surface at one end and having a hook or pin 67 at the opposite end to engage and spread the tissue proximate to the anastomosis site to improve the exposure of the target artery. The planar surface 62 is attached to a post 69 which may be attached to a stable support such as the rib retractor as shown in FIG. 9b. The planar surface 62 may also have at least one port 70 for receiving a suture line.

Figure 8:
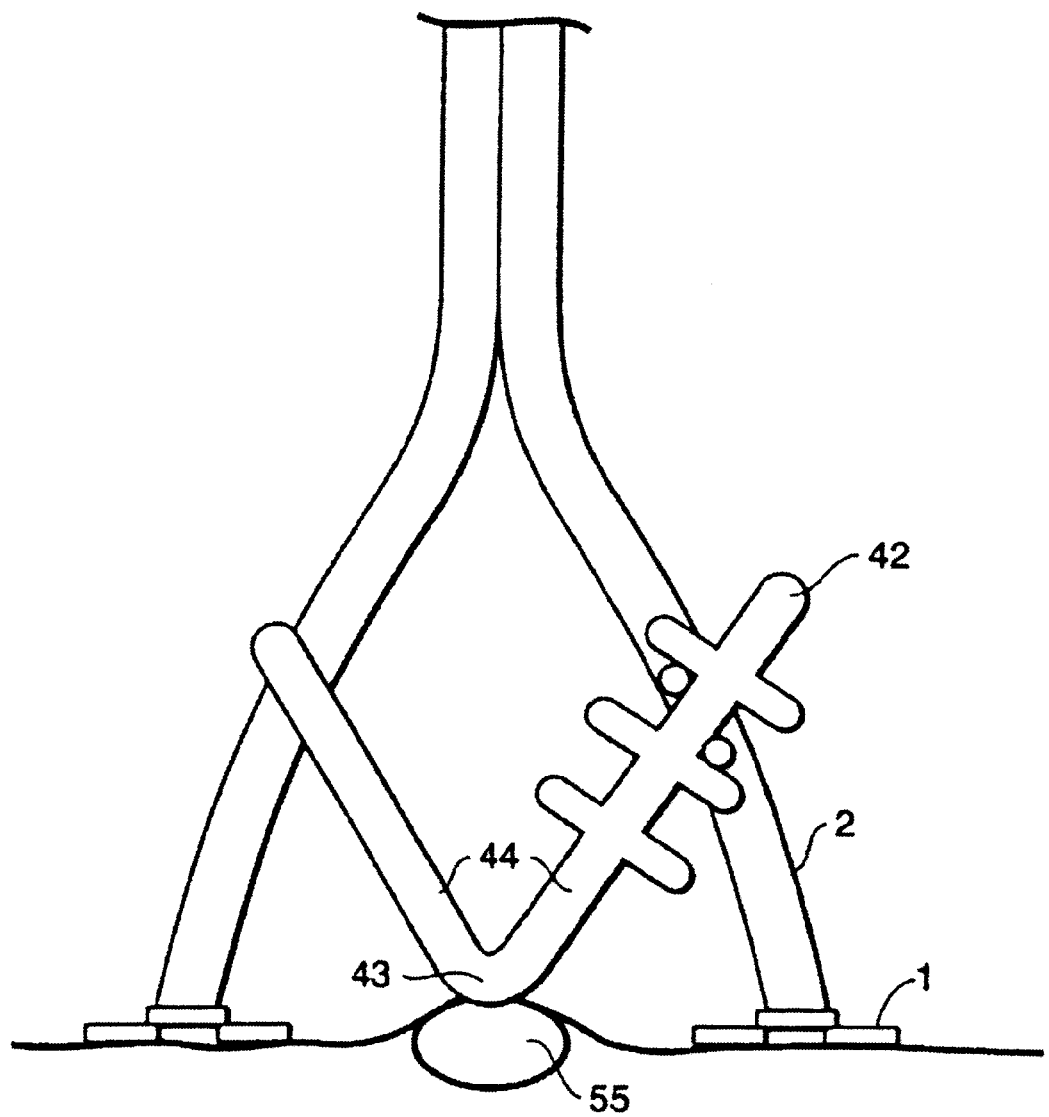
FIG. 8 is a stabilizing contact member having means associated therewith for attaching a snap fixture or other method of attachment to the stabilizing member such that the cardiac tissue is attached to the contact member.

Referring to FIG. 8, the stabilizing means may have operably associated therewith an artery occluder 42, which is preferably attached to the contact members 1 or to the connecting shaft 2. The artery occluder 42 may comprise a semi-rigid member which has a blunt portion 43, which may be positioned such that the blunt portion 43 engages the target artery 55 and compresses the target artery 55 to a point causing occlusion of the target artery 55 passing between the contact members 1 such that the blood flow through the artery is substantially reduced or eliminated. Preferably, the occluder 42 has a shaft portion 44 which traverses the connection shaft 2 such that the blunt portion 43 of the occluder 42 may move from above the level of the target artery 55 to a point sufficient to occlude the blood flow.

Figure 9A:
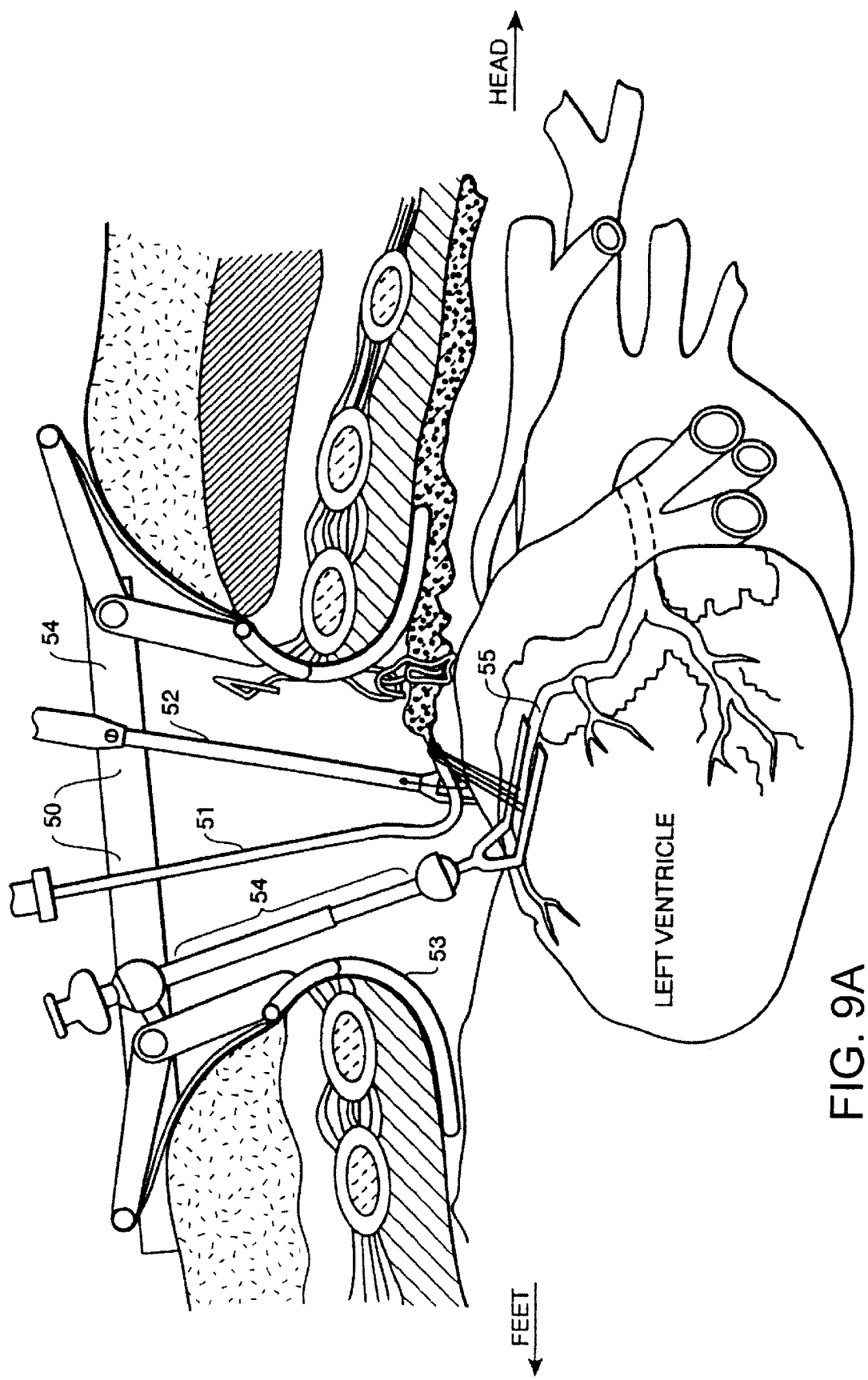
FIG. 9A is a view of the interior of the chest cavity during a CABG procedure on the beating heart with the stabilizing means operably associated with a retractor and being used in conjunction with other surgical apparatus to facilitate completing the anastomosis.
Figure 9B:
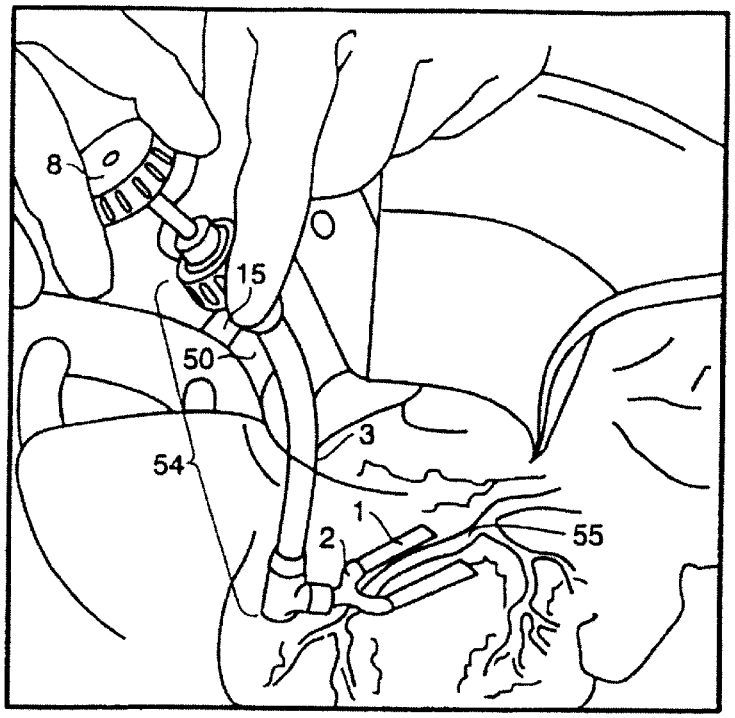
FIGS. 9B and 9C show the stabilizing means of the invention having been introduced through a thoracotomy to contact the beating heart to engage the heart tissue on either side of a target coronary artery to which an anastomosis is sewn.

Referring to FIG. 9A, the means for stabilizing the beating heart 54 of the invention is shown in use together with a rib retractor 50 and additional apparatus 51, 52 which may be used during the beating heart CABG procedure. In use, the blades 53 of the retractor separate the ribs, thereby providing an access space for the introduction of surgical instruments, including the stabilizing means 54 of the invention. The stabilizing means 54 is thus brought into contact with the heart such that the contact members are proximate to the target artery 55. Once the stabilizing force has been exerted, sufficient to minimize the motion of the beating heart, the stabilizing means 54 is fixed in place, preferably by attachment to the rib retractor 50.

Referring to FIG. 9B, the stabilizing means 54 is an embodiment substantially as described above and shown in FIG. 1 which comprises a pair of rectangular, substantially planar contact members 1 which are placed proximate to a target artery 55. The shaft means 3 is conformable such that it may be conveniently attached to the rib retractor 50. As shown in FIG. 9B, the surgeon may readily adjust the orientation and positioning of the contact members 1 relative to the shaft means 3 while the stabilizing means 54 is in continuous contact with the heart by manipulating the thumbscrew 8 at the proximal end of the instrument.

Figure 9C:
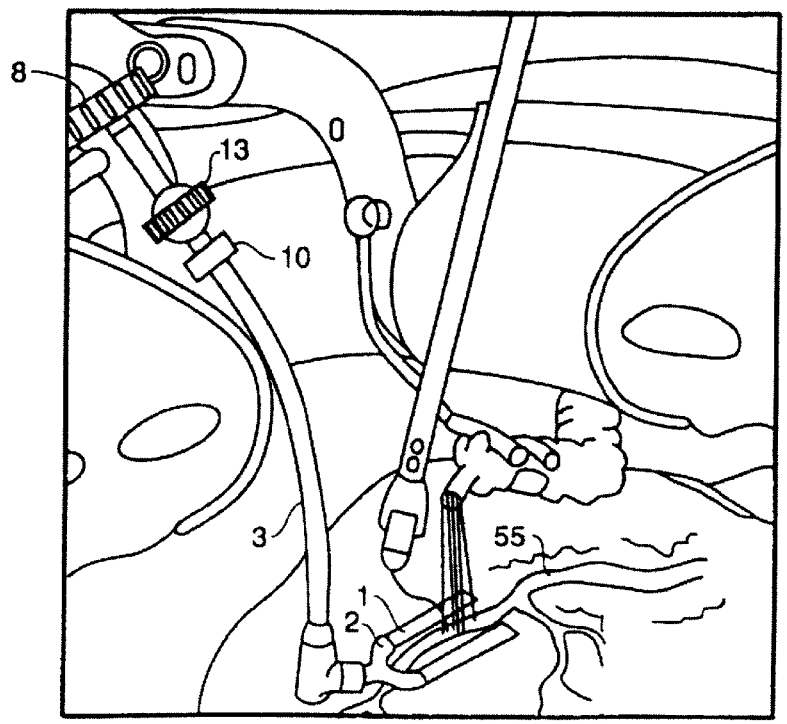

FIG. 9c shows a later stage of the procedure at a point where the anastomosis is being completed by suturing at target artery 55. The stabilizing means 54 thus maintains a stabilizing force at the anastomosis site for the duration of the procedure.

Figure 10:
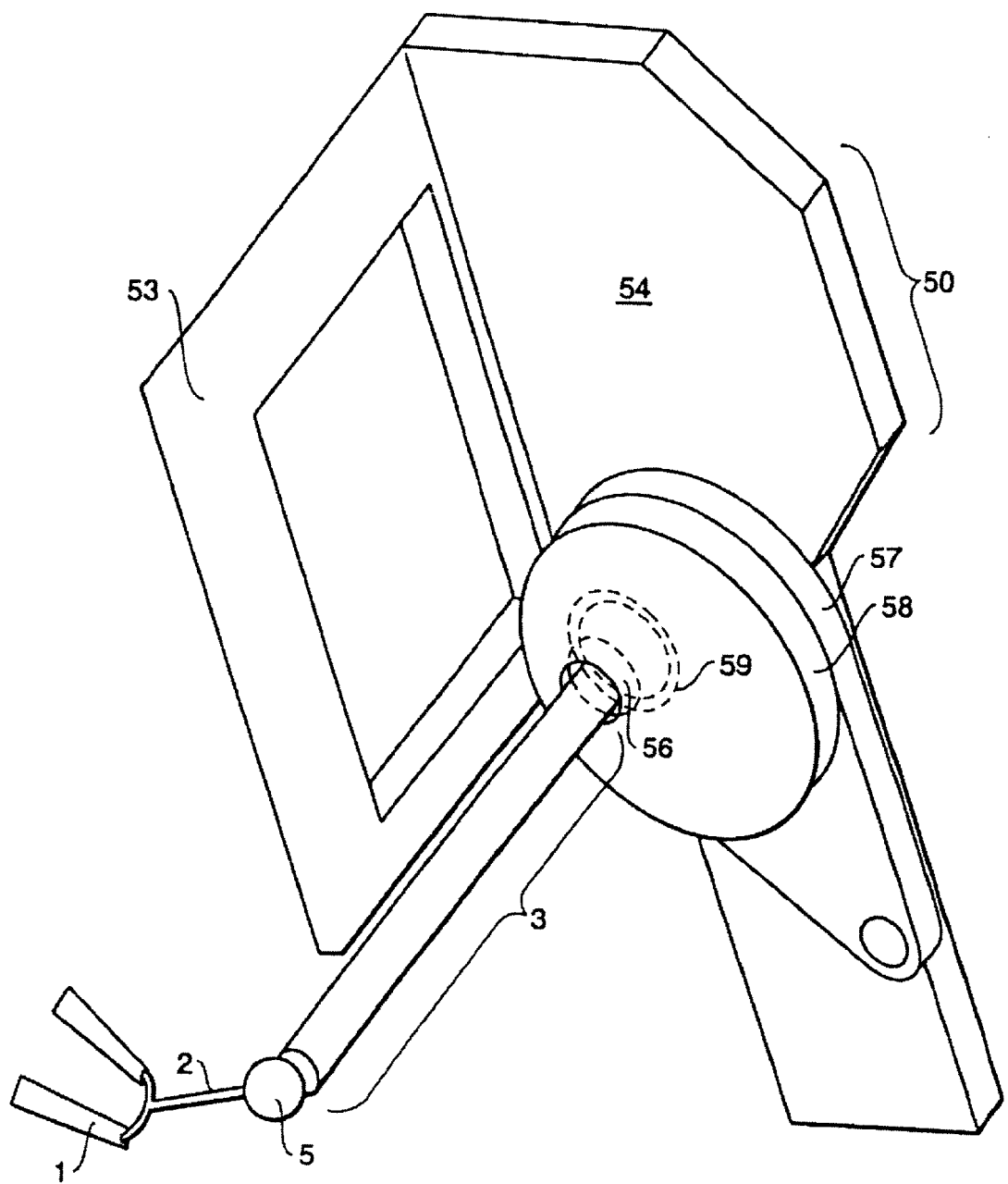
FIG. 10 is an embodiment of the stabilizing means of the invention having a pair of plates operably associated with a rib retractor and a sphere disposed between the plates to facilitate orientation of the shaft means.

Referring to FIG. 10, as noted above, attachment to a rib retractor is a preferred technique for fixing the position and orientation of the stabilizing means. The stabilizing means of the invention may therefore advantageously be attached to a fixture attached to a rib retractor 50 or may be configured to be directly incorporated into the body of a portion of the rib retractor 50.

A surgical rib retractor 50 is generally comprised of a body 54 having blades 53 attached thereto, which engage the ribs and spread the ribs when the retractor 50 is operated to move the blades 53 apart from one another. The space created by the retracted blades 53 provides access to the heart. Thus, once the retractor 50 is locked into the open position, the stabilizing means may be applied to the heart and a stabilizing force maintained at the site of the anastomosis by fixing the position and orientation of the shaft means 3 relative to the rib retractor 50. Referring to FIG. 10, the shaft means 3 traverses the width of the body 54 of the retractor 50 and is held in place by an upper plate 57 and a lower plate 58 having circular openings 59 therein through which the shaft means 3 passes and which maintain the position of a sphere 56 positioned between the upper plate 57 and lower plate 58. The size of the openings 59 is larger than the diameter of the shaft means 3 but smaller than the largest diameter of the sphere 56. Thus, the shaft means 3 passes through the sphere 56 and may pivot about a point approximately at the center of the sphere 56.

Figure 11:
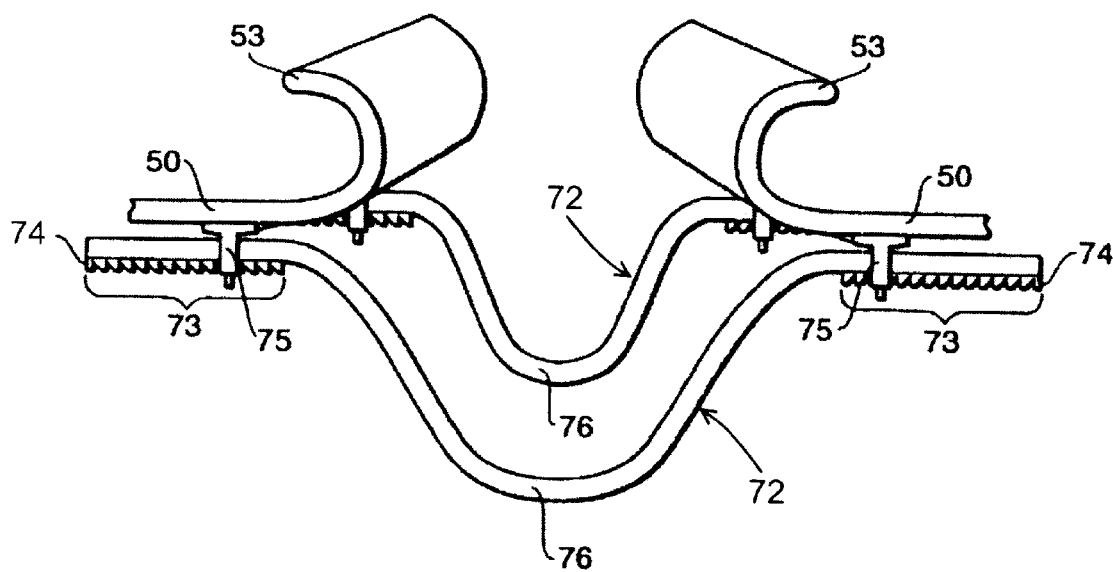
FIG. 11 is an embodiment of the stabilizing means of the invention having stabilizer bars suspended from the bottom side of a rib retractor wherein the stabilizer bars engage a ratchet means.
Figure 12:
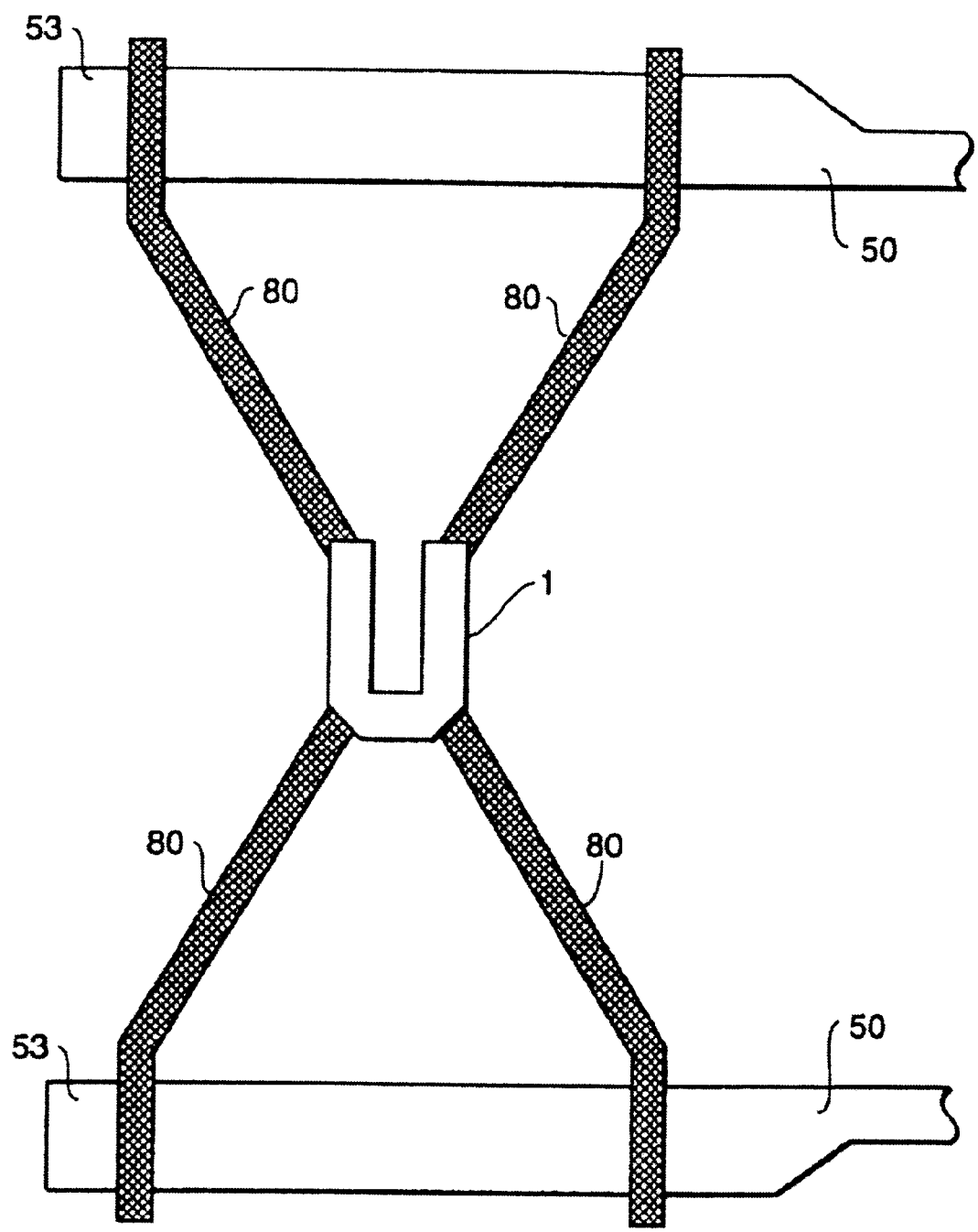
FIG. 12 is an embodiment of the invention having malleable supports attached at the ends on the contact members and attached to the rib retractor.

Referring to FIGS. 11 and 12, because the available access and working space for the surgeon may be limited, certain embodiments of the invention may be contained substantially within the chest cavity. Preferably, the stabilizing means is connected to the bottom of the rib retractor 50 on each side of the opening created by spreading the ribs using the rib retractor 50.

Referring to FIG. 11, rib retractor 50 is shown in an open position whereby blades 53 engage and spread the ribs. A pair of stabilizing bars 72 having a conventional ratchet means 73 formed at the ends thereof are positioned beneath the retractor. The ratchet means 73 comprised of a plurality of teeth 74 on the stabilizing bars 72 and a ratcheting aperture 75 permitting one-way passage of the stabilizing bars 72 unless released by a release mechanism. The stablizing bars 72 are curved downward such that as the bars are advanced through the ratchet means 73, the lowermost portion 76 of the stablizing bars 72 engages the beating heart proximate to the anastomosis site.

Referring to FIG. 12, the orientation of the portion of the stabilizing means which engages the heart relative to the rib retractor 50 is similar to the embodiment shown in FIG. 11. In this embodiment, a contact member 1 is attached on opposite ends to at least two malleable supports 80 which are in turn attached to the rib retractor 50. The malleable supports 80 are preferably made of stainless steel bands which are woven in a mesh or have a repeating serpentine configuration to allow for substantial expansion within the chest cavity. This configuration yields a malleable support 80 with sufficient tensile strength to maintain a stabilizing force at the anastomosis site while allowing the surgeon to manipulate the malleable supports within the chest cavity to achieve the desired orientation relative to the beating heart.

The particular examples set forth herein are instructional and should not be interpreted as limitations on the applications to which those of ordinary skill are able to apply this invention. Modifications and other uses are available to those skilled in the art which are encompassed within the spirit and scope of the following claims.

What is claimed is:

1. A device for use in cardiovascular surgery on a beating heart, comprising:
    a shaft means having a distal end and a proximal end;
    a stabilizing member adapted to engage a surface of the beating heart; and
    a ball-joint connecting said shaft means and said stabilizing member, said ball-joint allowing said stabilizing member to be positioned about three degrees of freedom relative to said shaft means.

2. The device of claim 1, wherein said stabilizing member is freely moveable about said ball-joint when in a first condition, and is locked relative to said ball-joint when in a second condition.

3. The device of claim 1, wherein said shaft means is a shaft.

4. The device of claim 3, wherein said shaft is substantially rigid.

5. The device of claim 1, wherein said shaft means is a curved tubular member.

6. The device of claim 5, wherein said curved tubular member is substantially rigid.

7. The device of claim 5, wherein said stabilizing member comprises a substantially planar base section having a central aperture.

8. The device of claim 1, wherein said shaft means is a flexible member having a plurality of interconnecting links.

9. The device of claim 1, wherein said stabilizing member is substantially U-shaped.

10. The device of claim 1, wherein said stabilizing member comprises a substantially planar base section having a central aperture.

11. The device of claim 10, wherein said stabilizing member further comprises at least one opening adapted to receive and hold a suture or other flexible support line.

12. The device of claim 11, wherein said at least one opening comprises at least one slot.

13. The device of claim 11, wherein said at least one opening comprises at least one hole.

14. The device of claim 10, wherein said stabilizing member further comprises a side opening in said substantially planar base section extending into said central aperture.

15. A device for use in cardiovascular surgery on a beating heart, comprising:
    a curved tubular member having a distal end and a proximal end, said tubular member being curved along a substantial portion of its length between said distal end and said proximal end; and
    a stabilizer member connected to said distal end, said stabilizer member adapted to engage the surface of the beating heart for localized stabilizatin of an area where a surgical procedure is to be performed.

16. The device of claim 15, further comprising a ball-joint connecting said curved tubular member and said stabilizing member.

17. The device of claim 16, wherein said ball-joint allows said stabilizing member to be positioned about three degrees of freedom relative to said curved tubular member, said ball-joint further being lockable so as to prevent movement of said stabilizing member relative to said curved tubular member when said ball-joint is in a locked condition.

18. The device of claim 16, further comprising a locking mechanism movably mounted to said curved tubular member, said locking mechanism being movable relative to said curved tubular member to abut against said ball-joint thereby locking a position of said ball-joint.

19. The device of claim 15, further comprising an anchor portion attachable to said curved tubular member and to a stationary object.

20. The device of claim 19, wherein the stationary object is a retractor.

21. The device of claim 15, wherein said stabilizer member comprises a rigid retaining element having an aperture exposing an artery at an operative site, the retaining element further including planar compression surface regions on opposite sides of the aperture.

22. The device of claim 21, wherein the retaining element comprises a planar section surrounding the aperture.

23. The device of claim 21, wherein the retaining element comprises a side opening in a base section extending into the aperture.

24. A device for use in cardiovascular surgery on a beating heart, comprising;

a shaft means having a distal end and a proximal end; and a stabilizing member connectable to said shaft means and adapted to engage a surface of the beating heart, said stabilizing member having a substantially rigid heart contacting surface adapted to contact and stabilize a portion of the heart without application of a vacuum, and an aperture that exposes an operative site, the aperture extending along a longitudinal axis of the stabilizing member.

* * * * *

UNITED STATES PATENT AND TRADEMARK OFFICE
CERTIFICATE OF CORRECTION

PATENT NO.   : 6,315,717 B1                                             Page 1 of 1
DATED        : November 13, 2001
INVENTOR(S)  : Benetti, Federico J. et al.

It is certified that error appears in the above-identified patent and that said Letters Patent is hereby corrected as shown below:

Column 5,
Line 66, change "at" with -- of --;

Column 9,
Line 6, delete "and";

Column 10,
Line 63, after the word "coronary" please insert -- artery --.

Signed and Sealed this

Twenty-eighth Day of January, 2003

JAMES E. ROGAN
*Director of the United States Patent and Trademark Office*